(12) United States Patent
Velagaleti et al.

(10) Patent No.: US 10,207,003 B2
(45) Date of Patent: *Feb. 19, 2019

(54) LIQUID PENTABLOCK CO-POLYMER FORMULATIONS FOR SUSTAINED DELIVERY OF THERAPEUTICS

(71) Applicant: i-novion, Inc., Randolph, NJ (US)

(72) Inventors: Poonam R. Velagaleti, Randolph, NJ (US); Brian C. Gilger, Raleigh, NC (US); Ulrich Grau, Ueberlingen (DE); Rasidul Amin, Cary, NC (US); Santhi Abbaraju, Cary, NC (US)

(73) Assignee: inovion, Inc., Randolph, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/582,685

(22) Filed: Apr. 29, 2017

(65) Prior Publication Data

US 2017/0312369 A1    Nov. 2, 2017

Related U.S. Application Data

(60) Provisional application No. 62/330,010, filed on Apr. 29, 2016, provisional application No. 62/456,921, filed on Feb. 9, 2017.

(51) Int. Cl.
| | |
|---|---|
| *A61K 9/00* | (2006.01) |
| *A61K 47/34* | (2017.01) |
| *A61K 9/10* | (2006.01) |
| *A61K 31/542* | (2006.01) |
| *A61K 31/573* | (2006.01) |
| *A61K 38/13* | (2006.01) |

(52) U.S. Cl.
CPC ............ *A61K 47/34* (2013.01); *A61K 9/0019* (2013.01); *A61K 9/0048* (2013.01); *A61K 9/10* (2013.01); *A61K 31/542* (2013.01); *A61K 31/573* (2013.01); *A61K 38/13* (2013.01)

(58) Field of Classification Search
CPC .... A61K 31/542; A61K 31/573; A61K 38/13; A61K 47/34; A61K 9/0019; A61K 9/0048; A61K 9/10
See application file for complete search history.

(56) References Cited

U.S. PATENT DOCUMENTS

| | | | |
|---|---|---|---|
| 5,702,717 A | 12/1997 | Cha et al. | |
| 8,551,531 B2 * | 10/2013 | Mitra ................. | A61K 9/0019 424/497 |
| 8,980,839 B2 | 3/2015 | Mitra et al. | |
| 9,011,927 B2 * | 4/2015 | Mitra ................. | A61K 9/0019 424/497 |
| 9,611,353 B2 * | 4/2017 | Mitra ................. | C08G 63/912 |
| 2011/0250283 A1 | 10/2011 | Mitra et al. | |
| 2014/0017175 A1 | 1/2014 | Mitra et al. | |
| 2016/0090444 A1 | 3/2016 | Mitra et al. | |
| 2017/0326072 A1 | 11/2017 | Velagaleti et al. | |

FOREIGN PATENT DOCUMENTS

| | | |
|---|---|---|
| WO | 2013/055331 | 4/2013 |
| WO | 2014/186669 A1 | 11/2014 |
| WO | 2017/190114 A1 | 11/2017 |
| WO | 2017/190115 A1 | 11/2017 |

OTHER PUBLICATIONS

Di Tommaso, et al., "Ocular biocompatibility of novel Cyclosporin A formulations based on methoxy poly(ethylene glycol)-hexylsubstituted poly(lactide) micelle carriers", International Journal of Pharmaceutics, vol. 416, pp. 515-524 (2011).
Kulthe, et al., "Mixed micelle formation with hydrophobic and hydrophilic Pluronic block copolymers: Implications for controlled and targeted drug delivery", Colloids and Surfaces B: Biointerfaces, vol. 88, pp. 691-696 (2011).
Mondon, et al., "Novel Cyclosporin A formulations using MPEG—hexyl-substituted polylactide micelles: A suitability study", European Journal of Pharmaceutics and Biopharmaceutics, vol. 77, pp. 56-65 (2011).
Patel et al. "Tailor-Made Pentablock Copolymer Based Formulation for Sustained Ocular Delivery of Protein Therapeutics", Journal of Drug Delivery, vol. 2014, Art. 401747, Jun. 22, 2014, pp. 1-15.
Schaefer et al. "Sustained Release of Protein Therapeutics from Subcutaneous Thermosensitive Biocompatible and Biodegradable Pentablock Copolymers (PTSgels)", Journal of Drug Delivery, vol. 2016, Art. 2407459, Jul. 25, 2016.
PCT International Search Report and Written Opinion for International Application No. PCT/US17/30311, dated Aug. 1, 2017.
Patel et al. "Novel Thermosensitive Pentablock Copolymers for Sustained Delivery of Proteins in the Treatment of Posterior Segment Diseases", Protein & Peptide Letters, vol. 21, No. 11, pp. 1185-1200, 2014.

(Continued)

*Primary Examiner* — Robert A Wax
*Assistant Examiner* — Olga V Tcherkasskaya
(74) *Attorney, Agent, or Firm* — Greenberg Traurig, LLP; David J. Dykeman; Fang Xie

(57) ABSTRACT

Provided herein are amphiphilic polymers compositions for making aqueous formulations. In one aspect, a solution composition for delivery and release of active ingredients comprises a block co-polymer having formula: PEG-PCL-PLA-PCL-PEG or PGA-PCL-PEG-PCL-PGA or PLA-PCL-PEG-PCL-PLA or PCL-PLA-PEG-PLA-PCL or PCL-PGA-PEG-PGA-PCL. The block co-polymers are biodegradable, stable and compatible with hydrophilic, hydrophobic, and combinations thereof, biologic or chemical active agents. In some embodiments, the block co-polymers enable sustained and/or continuous release of various active agents. In certain embodiments, the block co-polymers can be used to make an artificial tear preparation, a lubricant for joints or wound cover or adhesive.

15 Claims, 10 Drawing Sheets

(56) References Cited

OTHER PUBLICATIONS

Huang et al., "Synthesis and Characterization of Block Polymers of ε-Caprolactone and DL-Lactide Initiated by Ethylene Glycol or Poly(ethylene glycol)", Macromolecular Chemistry and Physics, vol. 204, Issue 16, pp. 1994-2001, Nov. 2003.

Kim et al., "The Synthesis and Biodegradable behavior of PLA-PCL-PEG-PCL-PLA Multi Block Copolymer", Polymer Preprints, 2000, vol. 49 No. 7 1557-1558.

Liu et al., "Themioreversible gel-sol behavior of biodegradable PCL-PEG-PCL triblock copolymer in aqueous solutions", Journal of Biomedical Materials Research, vol. 84B, Issue 1, pp. 165-175, Jan. 2008.

Patel et al., "Novel Pentablock Copolymer-Based Nanoparticulate Systems for Sustained Protein Delivery", AAPS Pharm Scitech, vol. 16, Issue 2, Oct. 16, 2014, pp. 1-15.

Tamboli et al., "Novel pentablock copolymer (PLA-PCL-PEG-PCL-PLA) based nanoparticles for controlled drug delivery: Effect of copolymer compositions on the crystallinity of copolymers and in vitro drug release profile from nanoparticles", Colloid Polymer Science, vol. 291, Issue 5, May 1, 2013, pp. 1235-1245.

International Search Report and Written Opinion for corresponding International Application No. PCT/US17/30312, dated Aug. 4, 2017.

* cited by examiner

Day 0

Day 21

PTS 1-0GH (4°C)
 20%    15%      10%    5%

PTS 121GH (4°C)
 20%    15%      10%   5%

PTS 1-0GH (Room Temperature)

PTS 121GH (Room Temperature)

LIQUID PENTABLOCK CO-POLYMER FORMULATIONS FOR SUSTAINED DELIVERY OF THERAPEUTICS

CROSS-REFERENCE TO RELATED APPLICATIONS

This application claims priority to and the benefit of U.S. Provisional Application Nos. 62/330,010 filed Apr. 29, 2016 and 62/456,921 filed Feb. 9, 2017, the entire disclosures of which applications are incorporated herein by reference.

FIELD

The compositions and methods disclosed herein relate to biodegradable, biocompatible and amphiphilic pentablock co-polymers, specifically aqueous formulations that are useful for sustained delivery of hydrophobic and hydrophilic therapeutics.

BACKGROUND

Various block polymer compositions are known in the art. For example, triblock polymers such as the PCL-PEG-PCL and PLA-PEG-PLA triblock polymers comprised of poly-ethylene glycol (PEG) and poly(ε-caprolactone) (PCL), and polylactide (PLA) are disclosed by Cha et al., U.S. Pat. No. 5,702,717 and Lui et al. (Thermoreversible gel-sol behavior of biodegradable PCL-PEG-PCL triblock copolymer in aqueous solutions, J. Biomed. Mater. Res. B. Appl. Biomater., January, 2008, 84 (1) 165-75). The individual polymers forming the block polymer are all well-known, FDA-approved, biodegradable, and biocompatible materials.

In addition, the pentablock co-polymer PLA-PCL-PEG-PCL-PLA has been studied by Deng et al. (Synthesis and Characterization of Block Polymers of ε-Caprolactone and DL-Lactide Initiated by Ethylene Glycol or Poly (ethylene glycol), J. Polymer Sci., 1997, Vol 35 No. 4 703-708); Kim et al. (The Synthesis and Biodegradable behavior of PLA-PCL-PEG-PCL-PLA Multi Block Copolymer, Polymer Preprints, 2000, Vol. 49 No. 7 1557-1558). These insoluble polymers were proposed as tissue scaffolds by Huang (Polymeres Bioresorbables Derives de Poly(ε-caprolactone) en Ingénierie Tissulaire, Centre de Recherche surles Biopolyméres Artificiels, UMR CNRS 5473 Faculté de Pharmacie, Université Montpellier I en collaboration avec Division de Bioingénierie, Université Nationale de Singapour).

Pentablock co-polymer compositions described to form nanoparticles with a bioactive agent are disclosed by U.S. Pat. No. 8,551,531, PCT Publication No. WO2014/186669, and Patel et al. (Novel Thermosensitive Pentablock Copolymers for Sustained Delivery of Proteins in the Treatment of Posterior Segments Diseases, (2014) pp. 1185-1200), all of which are incorporated herein by reference. However, currently available compositions are typically only compatible with either hydrophobic or hydrophilic active agents, not both. Furthermore, hydrophobic active agents and combinations of hydrophilic and hydrophobic active agents can be difficult to formulate, in particular in the form of clear, aqueous solutions. Therefore, a need exists for improved aqueous formulations that can deliver various active agents to patients in need thereof.

SUMMARY

The present disclosure, in one aspect, is directed to compositions of amphiphilic pentablock co-polymers (PTSsol) useful for the aqueous formulations of hydrophilic and/or hydrophobic active ingredients, such as biologics and small molecule drugs useful in the treatment or diagnosis of a variety of disorders or diseases. In some embodiments, the compositions disclosed herein can be used for sustained release of such active ingredients in liquid formulation over a prolonged period of time. The amphiphilic pentablock co-polymers when dispersed in aqueous medium, can include small size particles (e.g., <1 μm in diameter) and may be, without wishing to be bound by theory, micellar in nature, and are suitable for sustained drug release of small molecule drugs and biologicals through various routes of administration. The polymers can be thermosensitive in nature. In some embodiments, the compositions can be such that they are liquid at about 4° C. and may only become slightly more viscous at body temperature (about 37° C.) but do not visibly gel which is highly desirable for the liquid formulations. For example, if used for topical application on ocular surface, the compositions disclosed herein can extend the release time of active ingredients (e.g., hydrophobic drugs that are especially difficult to solubilize) to, e.g., 1-48 hours and longer, compared to 5 minutes or less without the pentablock co-polymer compositions herein. When applied topically to the eye, the small size particles loaded with a drug can easily penetrate ocular surface and deliver drug in sufficient concentration to the back of the eye to be of therapeutic value. If injected intravitreal in the eye, intra articular in the knee or other joints, or intravenous for systemic circulation, the compositions disclosed herein can extend the release time of active ingredients to, e.g., at least 1 day and up to 6 months and longer. Other sustained release applications include topical application on dermal surface (e.g., for psoriasis or burn wounds) and subcutaneous injection.

In particular, one aspect of the present disclosure provides a composition for delivery of an active ingredient, comprising a co-block polymer having the formula of PEG-PCL-PLA-PCL-PEG in the form of an aqueous solution, wherein PEG is polyethylene glycol and has an average molecular weight of about 100 to about 10,000 Da and a molecular weight percentage of at least 25%, wherein preferably PEG has an average molecular weight of about 500 to about 5,000 Da; wherein PCL is poly(ε-caprolactone) and has an average molecular weight of about 100 to about 3000 Da, preferably about 200 to about 2000 Da, and more preferably about 300 to about 1500 Da; wherein PLA is polylactic acid and has average molecular weight of about 100 to about 5,000 Da, preferably about 150 to about 3000 Da, and more preferably about 200 to about 1500 Da; and wherein the polymer preferably has a total molecular weight of about 1,500 to about 20,000 Da, more preferably about 2,000 to about 15,000 Da, even more preferably about 2,500 to about 10,000 Da.

In another aspect, a composition is provided for delivery of an active ingredient, comprising a co-block polymer having the formula of PGA-PCL-PEG-PCL-PGA in the form of an aqueous solution, wherein PEG is polyethylene glycol and has an average molecular weight of about 100 to about 10,000 Da and a molecular weight percentage of at least 25%, wherein preferably PEG has an average molecular weight of about 500 to about 5,000 Da; wherein PCL is poly(ε-caprolactone) and has an average molecular weight of about 100 to about 3000 Da, preferably about 200 to about 2000 Da, and more preferably about 300 to about 1500 Da; wherein PGA is polyglycolic acid and has average molecular weight of about 100 to about 5,000 Da, preferably about 150 to about 3000 Da, and more preferably about 200 to about 1500 Da; and wherein the polymer preferably has a total molecular weight of about 1,500 to about 20,000 Da, more preferably about 2,000 to about 15,000 Da, even more preferably about 2,500 to about 10,000 Da.

In some embodiments, the PTSsol polymers disclosed herein may increase in viscosity but do not visibly gel at, e.g., 37° C. (body temperature) or higher temperatures and are sometimes referred to as non-gelling polymers. The non-gelling polymer can be present in small or large amounts, e.g., at about 0.01 to about 50 wt % of liquid formulation, preferably about 1 to about 35 wt %, more preferably about 2 to about 25 wt %. The composition can further comprise an aqueous medium and an active ingredient that is hydrophobic or hydrophilic admixed therein. The aqueous medium is water in one example. The active ingredient can be present at about 0.01 wt % to about 50 wt %, preferably about 0.1 to about 30 wt %, more preferably about 0.2 to about 10 wt %. The active ingredient can be a biologic or chemical agent. The active ingredient can be hydrophobic or hydrophilic, or a mixture of hydrophobic and hydrophilic ingredients.

In certain embodiments, the composition can further comprise of gelling polymers wherein adding one or more of non-gelling polymers prevent gelation of the gelling polymers. The gelling polymers can be present in small or large amounts, e.g., at about 0.01 to about 25 wt % of the liquid formulation, preferably about 1 to about 15 wt %, more preferably about 2 to about 10 wt %. The non-gelling can be present at 0.01 to 49.9 wt % of liquid formulation. The composition can further comprise an active ingredient that is hydrophobic or hydrophilic and is dissolved or dispersed in the polymers.

In a further aspect, an artificial tear comprising an aqueous solution of any of the compositions disclosed herein is provided. The aqueous solution may, in some embodiments, include one or more of amphiphilic polymer excipients, tonicity agents, buffers, sugars selected from trehalose, mannose, D-galactose, and lactose, preservatives, co-solvents or antioxidants. The aqueous solution can have a pH ranging from about 5.0 to about 8.0, preferably about 6.6 to about 7.4, and more preferably about 7.0.

Another aspect relates to a method for preparing an aqueous formulation of a hydrophobic active ingredient, comprising: dissolving or dispersing the hydrophobic active ingredient in a gelling polymer, and admixing with any composition containing a non-gelling polymer as disclosed herein, wherein the gelling polymer can be present at about 0.01 to about 25 wt % of the liquid formulation, preferably about 1 to about 15 wt %, more preferably about 2 to about 10 wt %.

Also, provided herein is a method of delivering an active ingredient to a mammal in need thereof, comprising: providing any composition disclosed herein admixed with an active ingredient, wherein the polymer is present at between about 0.01 wt % and about 50 wt % of the liquid formulation, preferably about 1 to about 35 wt %, more preferably about 2 to about 25 wt %; wherein the composition is in the form of a clear or near clear dispersion; and administering the composition to a mammal. In some embodiments, said administering is by a topical, oral or parenteral route.

In certain embodiments, the polymer disclosed herein bio-degrades or clears at a rate substantially similar to release rate of an active ingredient, allowing for repeat applications without interfering biologically or physically with a prior application. The polymer may biodegrade successively into substituent blocks, which are not substantially physiologically harmful, and wherein the polymer and the substituent blocks from biodegradation are tolerated in vivo such that long-term or repeat applications are feasible.

In some embodiments, the particle size (in diameter) of the polymer of the present disclosure in aqueous medium as determined by DLS (Dynamic light scattering) can range from about 5 nm to about 1 µm, preferably about 7-200 nm, more preferably about 10-100 nm, and most preferably less than about 30 nm. This is a particle size that normally escapes the typical response of the body's immune system by being able to avoid phagocytosis and has enhanced permeability through biological membranes. Thus, PTSsol dispersed in aqueous medium, are comprised of small size particles of amphiphilic in nature with high drug loading capacity of both hydrophobic and hydrophilic drugs that are suitable for sustained drug release of small drug molecules and biologicals through various routes of administration. In addition, the polymers described are biocompatible and biodegradable.

BRIEF DESCRIPTION OF THE DRAWINGS

The present technology will be further explained with reference to the attached drawings. The drawings shown are not necessarily to scale, with emphasis instead generally being placed upon illustrating the principles of the present disclosure.

Figure 1:
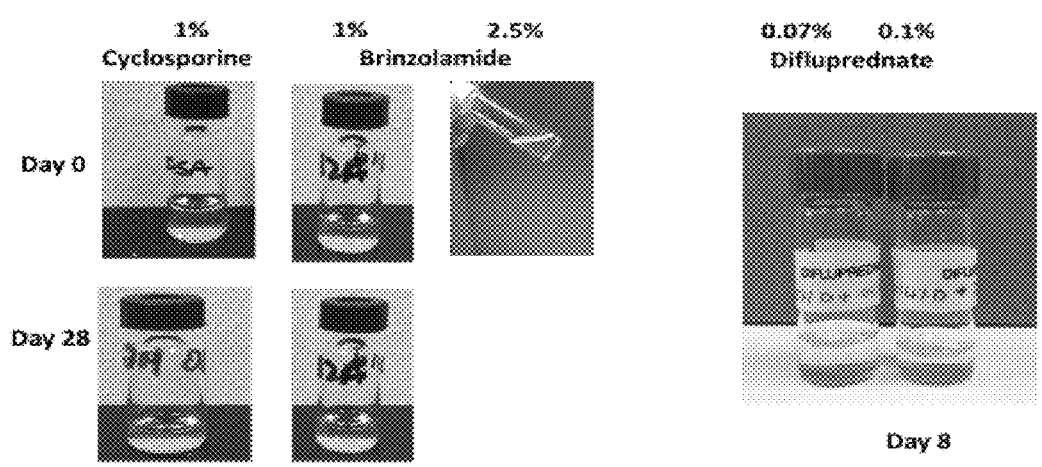
FIG. 1, left panel illustrates clear aqueous formulation for 1% and 2.5% brinzolamide and 1% cyclosporine A combined with an exemplary PTSsol at Day 0 and Day 28. The formulations remained visibly clear, when stored refrigerated for 28 days without drugs precipitating out. Right panel illustrates an exemplary 0.07% and 0.1% difluprednate PTSsol after 8 days of storage under refrigerated conditions. The formulation remained visibly clear for 8 days without drug precipitating out.

While the above-identified drawings set forth certain exemplary embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure is directed to pentablock co-polymers useful for biodegradable and biocompatible aqueous drug delivery systems. The amphiphilic pentablock co-polymers described herein may be used for delivery, in particular the sustained delivery of biologics, or small molecules, irrespective of their hydrophobic or hydrophilic nature, contained therein. In some embodiments, the compositions disclosed herein can be used for sustained release of various active ingredients over a prolonged period of time. For example, if used for topical application on ocular surface, the compositions disclosed herein can extend the release time of active ingredients to, e.g., 1-48 and longer hours, compared to about 5 minutes or less without the pentablock co-polymer compositions herein. Topical ocular application of drugs in PTSsol has the potential to deliver drugs to the back of the eye in sufficient concentration to be of therapeutic value. If injected intravitreal in the eye or intra articular in the knee or other joints, the compositions disclosed herein can extend the release time of active ingredients to, e.g., at least 1 day and up to 6 months and longer. Other sustained release applications include topical application on dermal surface (e.g., for psoriasis or burn wounds) and subcutaneous injection. The compositions in some embodiments can also be provided for intra venous injection for systemic circulation for, e.g., chemotherapy (e.g., paclitaxel, doxorubicin, etc.) or organ transplant rejection (e.g., cyclosporin). The small size particles can easily avoid mononuclear phagocytic system and therefore drug can be delivered to the targeted site. The small size particles are formed just by dispersing the polymer in aqueous medium. It does not require intervention of an organic solvent and sonication etc.

Conventionally, liquid drops (e.g., solutions or suspensions) when applied to ocular surface last for only about 5 minutes or less. The liquid amphiphilic pentablock co-polymer formulation described herein, when applied topically to eye surprisingly becomes bioadhesive or viscous (possibly without blurring), significantly increases contact time (e.g., 1-48 hours and longer) with ocular surface and hence allows higher drug penetration into the eye. Another advantage, without wishing to be bound by theory, is that the liquid pentablock co-polymer formulation described herein appears to form micelles (typical particle size about 5-200 nm, about 10-100 nm or <1 μm in diameter that are present in the aqueous polymer dispersion) which will also help improve drug penetration into the eye. Typically eye drops (e.g., commercial Azopt®, a milky suspension of 1% brinzolamide which is used in glaucoma to reduce TOP in the eye) need to be applied 3 times a day. As shown in the Examples and as exemplary embodiments, the amphiphilic pentablock co-polymer formulation disclosed herein can be used to make clear solution of Brinzolamide (e.g., 2.5% as tested in dogs) and need to be applied for only once a day or less for better results compared to Azopt®. This is a significant improvement over the prior technology. In some embodiments, due to small particle size of amphiphilic nature of the compositions of the present disclosure, which would easily disperse in aqueous formulation without the help of organic solvents or sonication etc., evade elimination by immune system, high loading capacity of hydrophobic and/or hydrophilic drug, biocompatible and biodegradable, mucoadhesive and muco-penetratable nature, this results in a very unique sustained drug release formulation including but not limited to for topical, dermal, intravitreal or parenteral applications. Because the polymers disperse in aqueous medium as small size particles (<1 μM), penetration through ocular surface may deliver drugs to the back of the eye in significant concentration to be of therapeutic value.

The present disclosure is also directed to methods for fabricating the amphiphilic pentablock co-polymers disclosed herein, as well as compositions comprising the biodegradable and biocompatible pentablock co-polymers with hydrophilic and/or hydrophobic drugs, such as biologics or small molecule drugs, in particular in the form of aqueous solutions. The present disclosure is well adapted for the administration of the hydrophilic and hydrophobic drugs, or combinations thereof, particularly hydrophobic drugs that are generally difficult to solubilize.

Specifically, some hydrophobic drugs are known to be difficult to formulate in aqueous formulations and therefore, are formulated typically as emulsions or suspensions. Using the present disclosure, however, hydrophobic drugs can be formulated at significantly high drug concentrations as clear liquid in certain hydrophilic or in combination with non-gelling polymers disclosed herein. As a result, clinically relevant formulations can be generated for various applications, such as ocular, topical, oral, and/or parenteral delivery. These formulations are referred to as "PTSsol" in some embodiments. As demonstrated herein, in one example, 10% of 121GH polymer can dissolve cyclosporine (CsA) at 1% and Brinzolamide (BRZ) at 2.5% and result in very clear liquids. BRZ solutions stored at room temperature or refrigerated at 4° C. remained clear and stable for 8 weeks (or longer) of testing. Higher concentrations for CsA or BRZ are feasible. Similarly, PTSsol for celecoxib (0.5%) was prepared in 121GH.

All polymers are amphiphilic in nature. However, some hydrophobic drugs are very hydrophobic and do not directly dissolve in relatively more hydrophilic polymers (typical for PTSsol). In certain embodiments, these drugs (e.g., difluprednate) can first be dispersed in a very small amount of relatively more hydrophobic gelling polymer such as PTS 113GH or PTS 122GH and then can subsequently be mixed with relatively more hydrophilic PTS121GH to maintain the formulations as liquid at room temperature and at body temperature. Using this strategy PTSsol formulations for difuprednate was generated at 0.1% concentration. Higher concentrations are possible.

In various embodiments, the present technology can be used to prepare a formulation having a combination of both hydrophobic and hydrophilic drugs where desired. For example, this can be achieved by adding hydrophilic drug to PTSsol that has already been generated with the hydrophobic drug.

In some embodiments, PTSsol can be in the form of clear but polymeric dispersion of a mixture of molecular weight polymers (e.g., 1500-20,000), the polymers may stay at the surface of the administration to which they are applied for some length of time. Since the pentablock co-polymers appear to be bio-adhesive and are biocompatible and biodegradable, such a property can be very useful for applications such as preparing artificial tears for relieving eye discomfort caused by dry eye. In one example, PTS 121GH vehicle PTSsols with no drug added to have been prepared in PBS, pH 7.4 at 5-20% polymer concentration. These formulations remained clear for at least 21 days stored at room temperature as well as at 4° C. Specific drugs tested include 2.5% BRZ as small hydrophobic molecule in 25% 1-0 GH, as well as NIR-IgG as an example for biologics in 25% 121GH and 1-0GH.

PTSsol can be used in various therapeutic formulations such as eye drops for topical applications and sprays on the skin (e.g., for wound healing from burn or psoriasis and more indications). Since some PTSsol are clear solutions, they can also be used to, e.g., generate injectable formulations including but not limited to for systematic circulation of drugs that are not aqueous soluble otherwise. Because the polymers disperse in aqueous medium as small size particles (<1 μM), penetration through ocular surface may deliver drugs to the back of the eye in significant concentration to be of therapeutic value.

Definitions

For convenience, certain terms employed in the specification, examples, and appended claims are collected here. Unless defined otherwise, all technical and scientific terms used herein have the same meaning as commonly understood by one of ordinary skill in the art to which this disclosure belongs.

For convenience, certain terms employed in the specification, examples, and appended claims are collected here. Unless defined otherwise, all technical and scientific terms used herein have the same meaning as commonly understood by one of ordinary skill in the art to which this disclosure belongs.

The articles "a" and "an" are used herein to refer to one or to more than one (i.e., at least one) of the grammatical object of the article. By way of example, "an element" means one element or more than one element.

As used herein, the term "about" means within 20%, more preferably within 10% and most preferably within 5%. The term "substantially" means more than 50%, preferably more than 80%, and most preferably more than 90% or 95%.

As used herein, "a plurality of" means more than 1, e.g., 2, 3, 4, 5, 6, 7, 8, 9, 10, 11, 12, 13, 14, 15, 16, 17, 18, 19, 20, or more, e.g., 25, 30, 40, 50, 60, 70, 80, 90, 100, 200, 300, 400, 500, or more, or any integer therebetween.

As used herein, "administering" and similar terms mean delivering the composition to an individual being treated. Preferably, the compositions comprising the pentablock co-polymers of the present disclosure are administered by, e.g., parenteral, subcutaneous, intramuscular, transdermal, transmucosal, intra-articular, intrathecal, intraocular, intraperitoneal, intravenous, oral or topical routes.

As used herein, "biocompatible" refers to materials or the intermediates or end products of materials formed by solubilization, hydrolysis, or by the action of biologically formed entities which can be enzymes or other products of the organism and which cause no adverse effect on the body.

As used herein, "biodegradable" means that the pentablock co-polymer can break down or degrade within the body to non-toxic components after all bioactive agent or diagnostic agent has been released.

As used herein, "drug" or "active ingredient" shall refer to any biologic and/or chemical compound or substance adapted or used for a therapeutic purpose.

As used herein, an "effective amount" means the amount of bioactive agent or diagnostic agent that is sufficient to provide the desired local or systemic effect at a reasonable risk/benefit ratio as would attend any medical treatment or diagnostic test. This will vary depending on the patient, the disease, the treatment being effected, and the nature of the agent.

As used herein, "gel" or "gelling polymer" when used in reference to the pentablock co-polymers and/or drug combination at a temperature at or above the LCST (see below), shall be inclusive of such combinations are generally semi-solid in nature, such as those disclosed in U.S. Pat. No. 8,551,531, PCT Publication No. WO2014/186669 and U.S. Provisional Application No. 62/330,020 entitled "SUSTAINED RELEASE FORMULATION AND USE THEREOF" filed Apr. 29, 2016, all of which are incorporated herein by reference in their entirety. The term "gel" when used as a verb, refers to the process of forming a gel.

As used herein, "LCST" or "lower critical solution temperature," refers to the temperature at which the pentablock co-polymer undergoes reverse thermal gelation, i.e., the temperature below which the polymer is soluble in water and above which the pentablock polymer undergoes phase separation to form a semi-solid containing the drug and the pentablock polymer. The terms "LCST," "gelation temperature," and "reverse thermal gelation temperature," or the like shall be used interchangeably in referring to the LCST.

As used herein, "non-gelling polymer" refers to a polymer which is the same as gelling polymer at room temperature but having a LCST that is much higher than body temperature.

As used herein, "hydrophilic" refers to the ability to dissolve in water. When used in the context of the hydrophilic drugs or diagnostic agents in the present disclosure, the term embraces a drug that is preferably sparingly soluble, more preferably soluble, still more preferably freely soluble, and still most preferably very soluble, according to USP-NF definitions.

As used herein, "parenteral" shall mean any route of administration other than the alimentary canal and shall specifically include intramuscular, intraperitoneal, intra-abdominal, intra-articular, intra-ocular, subcutaneous, and intravenous.

As used herein, "pharmaceutically acceptable" shall refer to that which is useful in preparing a pharmaceutical composition that is generally safe, non-toxic, and neither biologically nor otherwise undesirable and includes that which is acceptable for veterinary use as well as human pharmaceutical use. Examples of "pharmaceutically acceptable liquid carriers" include water and organic solvents. Preferred pharmaceutically acceptable aqueous liquids include PBS, saline, and dextrose solutions etc.

As used herein, "peptide", "polypeptide", "oligopeptide," and "protein" shall be used interchangeably when referring to peptide or protein drugs and shall not be limited as to any particular molecular weight, peptide sequence or length, field of bioactivity, diagnostic use, or therapeutic use unless specifically stated.

As used herein, "solution," "aqueous solution," and the like, when used in reference to a combination of drug and pentablock co-polymer contained in such solution, shall mean a liquid-based solution having such drug/polymer combination dissolved or substantially uniformly suspended therein at a functional concentration and maintained at a temperature below the LCST of the block polymer.

As used herein, "thermosensitive" refers to a polymer which exists as a generally clear solution or dispersion near ambient temperature in water but when the temperature is raised to the LCST (which is preferably about body temperature for gelling polymers), interact to form a gel.

The term "treatment" or "treating" means administration of a drug for purposes including: (i) preventing the disease or condition, that is, causing the clinical symptoms of the disease or condition not to develop; (ii) inhibiting the disease or condition, that is, arresting the development of clinical symptoms; and/or (iii) relieving the disease or condition, that is, causing the regression of clinical symptoms.

Below, the exemplary embodiments are shown and specific language will be used herein to describe the same. It should nevertheless be understood that no limitation of the scope of the disclosure is thereby intended. Alterations and further modifications of the inventive features illustrated herein, and additional applications of the principles of the present disclosure as illustrated herein, for one skilled in the relevant art, in connection with this disclosure, should be considered within the scope of the present disclosure.

Biodegradable Thermosensitive Pentablock Co-Polymers

The present disclosure is directed to pentablock co-polymers comprised of (A) PLA, (B) PCL, (C) PEG, and/or (D) PGA. Generally, the co-block polymer will be an amphiphilic pentablock co-polymer, i.e., a CBABC, denoted as a "PEG terminal" arrangement or DBCBD type co-block polymer, denoted as a "PEG central" arrangement.

For preparation of the pentablock co-polymer used for the aqueous solutions of the present disclosure (PTSsol), in some embodiments, the pentablock co-polymer preferably has a PEG-PCL-PLA-PCL-PEG, "PEG terminal" configuration. In some embodiments, the pentablock co-polymer preferably has a PGA-PCL-PEG-PCL-PGA, PLA-PCL-PEG-PCL-PLA, PCL-PLA-PEG-PLA-PCL and/or PCL-PGA-PEG-PGA-PCL, "PEG central" configuration.

PEG Terminal Composition

For preparation of the pentablock polymer of the present disclosure, the pentablock co-polymer can have a "PEG Terminal" block configuration, comprising CBABC.

The hydrophobic A block segment is preferably derived from a L-lactide. The A block segment preferably comprises PLA having an average molecular weight of 100 to about 5,000 Da, preferably about 150 to about 3000 Da, and more preferably about 200 to about 1500 Da (for example, an average molecular weight of about 100 Da, 150 Da, 200 Da, 250 Da, 300 Da, 350 Da, 400 Da, 450 Da, 500 Da, 550 Da, 600 Da, 650 Da, 700 Da, 750 Da, 800 Da, 850 Da, 900 Da, 950 Da, 1000 Da, 1050 Da, 1100 Da, 1150 Da, 1200 Da, 1250 Da, 1300 Da, 1350 Da, 1400 Da, 1450 Da, 1500 Da, 1550 Da, 1600 Da, 1650 Da, 1700 Da, 1750 Da, 1800 Da, 1850 Da, 1900 Da, 1950 Da, 2000 Da, 2100 Da, 2200 Da, 2300 Da, 2400 Da, 2500 Da, 2600 Da, 2700 Da, 2800 Da, 2900 Da, 3000 Da, 3100 Da, 3200 Da, 3300 Da, 3400 Da, 3500 Da, 3600 Da, 3700 Da, 3800 Da, 3900 Da, 4000 Da, 4100 Da, 4200 Da, 4300 Da, 4400 Da, 4500 Da, 4600 Da, 4700 Da, 4800 Da, 4900 Da, 5000 Da, or some range therebetween). An average molecular weight in the range of about 200-1200 Da is most preferred. It will be appreciated that in the preferred embodiment, a linker separates the hydrophobic A block, but that the average molecular weight referenced for this block refers to the combined molecular weights of the PLA blocks on both sides of the linker.

The hydrophobic B block segment is preferably derived from a cyclic lactone, and is most preferably derived from ε-caprolactone. Thus, in one aspect, the B block segment comprises PCL having an average molecular weight of about 100 to about 3000 Da, preferably about 200 to about 2000 Da, and more preferably about 300 to about 1500 Da. For example, the B block segment is preferably PCL having an average molecular weight of about 100 Da, 200 Da, 300 Da, 400 Da, 500 Da, 600 Da, 700 Da, 800 Da, 900 Da, 1000 Da, 1100 Da, 1200 Da, 1300 Da, 1400 Da, 1500 Da, 1600 Da, 1700 Da, 1800 Da, 1900 Da, 2000 Da, 2100 Da, 2200 Da, 2300 Da, 2400 Da, 2500 Da, 2600 Da, 2700 Da, 2800 Da, 2900 Da, 3000 Da, or some range therebetween, and most preferably has an average molecular weight in the range of about 300-900 Da.

The hydrophilic C block segment is preferably PEG having an average molecular weight of about 100 to about 10,000 Da and a molecular weight percentage of at least 25%, wherein preferably PEG has an average molecular weight of about 500 to about 5,000 Da.

Thus, in one aspect, a pentablock co-polymers used to make the "PEG terminal" thermosensitive aqueous polymer in accordance with the present disclosure may be defined according to the following formula:

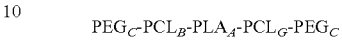

$$PEG_C\text{-}PCL_B\text{-}PLA_A\text{-}PCL_G\text{-}PEG_C$$

wherein PEG is polyethylene glycol and has an average molecular weight of about 100 to about 10,000 Da and a molecular weight percentage of at least 25%, wherein preferably PEG has an average molecular weight of about 500 to about 5,000 Da; wherein PCL is poly(ε-caprolactone) and has an average molecular weight of about 100 to about 3000 Da, preferably about 200 to about 2000 Da, and more preferably about 300 to about 1500 Da; wherein PLA is polylactic acid and has average molecular weight of about 100 to about 5,000 Da, preferably about 150 to about 3000 Da, and more preferably about 200 to about 1500 Da; and wherein the polymer preferably has a total molecular weight of about 1500 to about 20,000 Da, more preferably about 2000 to about 15,000 Da, even more preferably about 2500 to about 10,000 Da.

In some embodiments, different forms of PEG can be used, depending on the initiator used for the polymerization process. For example, the PEG can be methyl ether PEG (m-PEG). Different molecular weight (MW) combinations of m-PEG as a starting point can also be used. For example, the m-PEG can be a combination of two or more m-PEG having different MW ranging from 100-10000 Da, e.g., $MW_X + MW_Y$ such as MW 400+MW 550 at a 1:1 ratio or any other ratio. The polymers can also be combined after synthesis with m-PEG $MW_X$ and m-PEG $MW_Y$ separately.

A linker, such as diisocyanate, for example 1,4-diisocyanatebutate, 1,4-diisocynate phenylene, or hexamethylene diisocyanate can be included in the PEG terminal polymer.

By varying the molecular weights of the various A, B, and C blocks, the pentablock co-polymers synthesized as disclosed herein have various hydrophobic and hydrophilic blocks, which affect the molecular interactions with active agents, the release rate and duration of release of active agents, and the molecular characteristics of the polymer, such as the formation of an aqueous solution or the ability to achieve a gel composition. Further, the hydrophilic C block and the hydrophobic A and B blocks are synthesized and utilized because of their unique interactions with hydrophobic and hydrophilic active agents. Generally, for the preparation of aqueous compositions, the hydrophilic C block (PEG block) should be more than 25% by weight, the B block (PCL block) should be about or less than 50% by weight, and the A block (PLA block) should be about or less than 40% by weight.

The molecular weight of the water-soluble C block, relative to that of the hydrophobic A and B blocks, is regulated sufficiently high to retain desirable water-solubility and aqueous properties. In addition, for the preparation of aqueous solutions, the proportionate weight ratios of hydrophilic C block to the more hydrophobic A and B blocks must also be sufficient to enable the block polymer to be highly hydrophilic.

As shown in the following examples, the amphiphilic pentablock co-polymer compounds of the present disclosure are ideally suited to form composition, which may include an effective amount of active agents, such as biologics or small molecules. In general, the pentablock co-polymer can be designed to have a selected rate of drug release. However, the drug and/or diagnostic agent typically comprises about 0.01 to 50 wt % of the composition, more preferably about 0.1 to 30% wt of the composition, with about 0.2 to 10 wt % being most preferred.

PEG Central Composition

In some embodiments, the pentablock polymer preferably has a PGA-PCL-PEG-PCL-PGA or PLA-PCL-PEG-PCL-PLA or PCL-PLA-PEG-PLA-PCL or PCL-PGA-PEG-PGA-PCL configuration, denoted "PEG central."

For preparation of the pentablock polymer of the present disclosure, the pentablock polymer can have a "PEG Central" block configuration, comprising DBCBD.

The hydrophobic D block segment is preferably derived from a glycolide. The D block segment preferably comprises PGA or PLA having an average molecular weight of about 100 to about 5,000 Da, preferably about 150 to about 3000 Da, and more preferably about 200 to about 1500 Da (for example, the D block segment may have an average molecular weight of about 100 Da, 150 Da, 200 Da, 250 Da, 300 Da, 350 Da, 400 Da, 450 Da, 500 Da, 600 Da, 700 Da, 800 Da, 900 Da, 1000 Da, 1100 Da, 1200 Da, 1300 Da, 1400 Da, 1500 Da, 1600 Da, 1700 Da, 1800 Da, 1900 Da, 2000 Da, 2100 Da, 2200 Da, 2300 Da, 2400 Da, 2500 Da, 2600 Da, 2700 Da, 2800 Da, 2900 Da, 3000 Da, or some range therebetween). While the PGA segment is considered hydrophobic, it can be sufficiently hydrophilic to interact with hydrophilic drugs in some embodiments. The D block can also be PCL having an average molecular weight of about 100 to about 3000 Da, preferably about 200 to about 2000 Da, and more preferably about 300 to about 1500 Da.

The hydrophobic B block segment is preferably derived from a cyclic lactone, and is most preferably derived from ε-caprolactone. Thus, the B block segment comprises PCL having an average molecular weight of about 100 to about 3000 Da, preferably about 200 to about 2000 Da, and more preferably about 300 to about 1500 Da. The B block can also be PGA or PLA having an average molecular weight of about 100 to about 5,000 Da, preferably about 150 to about 3000 Da, and more preferably about 200 to about 1500 Da.

The hydrophilic C block segment is preferably PEG having an average molecular weight of about 100 to about 10,000 Da and a molecular weight percentage of at least 25%, wherein preferably PEG has an average molecular weight of about 500 to about 5,000 Da.

Thus, in one aspect, a pentablock polymers used to make an aqueous release polymer in accordance with the present disclosure may be defined according to the following formula:

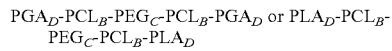
$PGA_D\text{-}PCL_B\text{-}PEG_C\text{-}PCL_B\text{-}PGA_D$ or $PLA_D\text{-}PCL_B\text{-}PEG_C\text{-}PCL_B\text{-}PLA_D$

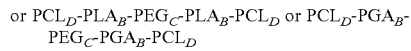
or $PCL_D\text{-}PLA_B\text{-}PEG_C\text{-}PLA_B\text{-}PCL_D$ or $PCL_D\text{-}PGA_B\text{-}PEG_C\text{-}PGA_B\text{-}PCL_D$ wherein PEG is polyethylene glycol and has an average molecular weight of about 100 to about 10,000 Da and a molecular weight percentage of at least 25%, wherein preferably PEG has an average molecular weight of about 500 to about 5,000 Da; wherein PCL is poly(ε-caprolactone) and has an average molecular weight of about 100 to about 3000 Da, preferably about 200 to about 2000 Da, and more preferably about 300 to about 1500 Da; wherein PLA is polylactic acid having an average molecular weight of about 100 to about 5,000 Da, preferably about 150 to about 3000 Da, and more preferably about 200 to about 1500 Da; wherein PGA is polyglycolic acid, having an average molecular weight of about 100 to about 5,000 Da, preferably about 150 to about 3000 Da, and more preferably about 200 to about 1500 Da; and wherein the polymer preferably has a total molecular weight of about 1500 to about 20,000 Da, more preferably about 2000 to about 15,000 Da, even more preferably about 2500 to about 10,000 Da.

By varying the molecular weights of the various B, C, and D blocks, the amphiphilic pentablock co-polymers synthesized as disclosed herein have various hydrophobic and hydrophilic blocks, which affect the molecular interactions with active agents, the release rate and duration of release of active agents, and the molecular characteristics of the polymer, such as the formation of an aqueous solution or the ability to achieve a gel composition. Further, the hydrophilic C block and the hydrophobic B and D blocks are synthesized and utilized because of their unique interactions with hydrophobic active agents. Generally, for the preparation of aqueous compositions, the hydrophilic C block (PEG block) should be greater than 25% by weight, the B block (PCL block) should be less than 50% by weight, and the D block (PGA or PLA block) should be less than 40% by weight.

The molecular weight of the water-soluble C block, relative to that of the hydrophobic B and D blocks, is regulated sufficiently high to retain desirable water-solubility and aqueous properties. In addition, for the preparation of aqueous solutions, the proportionate weight ratios of hydrophilic C block to the more hydrophobic B and D blocks must also be sufficient to enable the block polymer to be highly hydrophilic.

As shown in the following examples, the pentablock polymer compounds of the present disclosure are ideally suited to form composition, which may include an effective amount of active agents, such as biologics or small molecules. In general, the pentablock polymer can be designed to have a selected rate of drug release. However, the drug and/or diagnostic agent typically comprises about 0.01 to 50 wt % of the composition, more preferably about 0.1 to 30% wt of the composition, with about 0.2 to 10 wt % being most preferred.

Pentablock Polymer Properties

The mixture of the amphiphilic pentablock co-polymer used for non-gelling polymers and thermosensitive gelling polymers and the bioactive agent or diagnostic agent may be prepared as an aqueous dispersion of amphiphilic pentablock co-polymers. In general, this may be performed by forming a dispersion of the amphiphilic pentablock co-polymers and the bioactive agent or diagnostic agent at a suitable temperature.

The amphiphilic pentablock co-polymers and bioactive agent or diagnostic agent system will cause minimal toxicity and mechanical irritation to the surrounding tissue due to the biocompatibility of the materials and will be completely biodegradable within a specific predetermined time interval. The hydrophilic properties of the polymeric matrix can be controlled by proper formulation of the hydrophilic blocks or mixing gelling and non-gelling co-polymers in desirable proportions.

Pentablock Co-Polymer Applications

The biodegradable thermosensitive aqueous solutions comprising the amphiphilic pentablock co-polymers of the present disclosure provide for the aqueous delivery of hydrophilic and/or hydrophobic agents, such as a biologics or small molecule drugs. In general, the amphiphilic pentablock co-polymer can be designed to specifically not to instantly gel at body temperature (37° C.) (e.g., within minutes or hours (e.g., about 4 hours or less)) due to their hydrophilic nature. The pentablock co-polymer may gel in some cases in about 4 hours or longer and/or may become more viscous than at 4° C. Further, non-gelling pentablock co-polymers are useful in the preparation of aqueous compositions with hydrophobic active agents that do not easily formulate as aqueous compositions otherwise.

The biodegradable, thermosensitive amphiphilic pentablock co-polymers of the current disclosure can be formulated as pharmaceutical compositions, to be administered to a mammalian host, such as a human patient in a variety of forms, such as an aqueous composition. Suitable forms of polymer administration can include topical (ocular, dermal), injection or administration methods to regions such as: oral, intradermal, intravenous, subcutaneous, intramuscular, intravitreal, intraocular, intraarticular, intracardiac, intralesional, intraperitoneal, intracerebroventricular, intrathecal, intraosseous infusion, intracerebral, intrauterine, intravaginal, extraamniotic, intracavernous, and/or intravesica. The polymers of the present disclosure can be used as vitreous body substitutes, for example, for use in cataract surgery, retinal detachment surgery, and the like, as well as for ear treatments and oral treatments (e.g., dry mouth treatment).

The polymers can be administered by in liquid form, as dispersions. The polymers can be prepared in water, buffer solution, or optionally mixed with nontoxic surfactants, glycerol, sugars and other commonly used excipients. Under ordinary conditions of storage and use, these preparations contain a preservative to prevent the growth of microorganisms.

The amphiphilic pentablock co-polymers of the present disclosure are used to form stable, biodegradable, aqueous solutions. Active agents are generally used in the amphiphilic pentablock co-polymers, which are useful in a variety of therapeutic applications or diagnostic applications.

Therapeutic applications that can benefit from the use of amphiphilic pentablock polymers as a delivery vehicle can include, but not be limited to, the treatment of various conditions where therapeutics in the form of an aqueous formulation may be desired. For example, the polymer composition of the present disclosure can be utilized to deliver therapeutics for the treatment of: age related disorders (e.g., bone decalcification, menopause, joint degradation), cardiac disorders (e.g., atrial fibrillation), cancer treatment (i.e. chemotherapy, targeted cancer cell treatments), dermatological preparations and/or disorders (e.g., acne, dermal rashes or infections), immunosuppressants (e.g., tissue transplants, immune disorders), metabolic conditions (e.g., diabetes, obesity), muscular-skeletal conditions (e.g., anabolic/catabolic tissue stimulation, pain management, regeneration of tissue), oral treatments (e.g., dry mouth treatments, delivery of analgesics, antibiotics, or other agents), pain management (e.g., acute, chronic, or intermediate duration pain symptoms), psychiatric disorders (e.g., schizophrenia, bi-polar disorder, major depressive disorder), ophthalmic disorders (e.g., glaucoma, macular degeneration) and arthritis.

Exemplary therapeutics that can benefit from the use of amphiphilic pentablock co-polymers as the polymer composition of the present disclosure can include various hydrophobic drugs, hydrophilic drugs, or combinations of hydrophobic and hydrophilic drugs. For example, the polymer composition can be utilized to deliver therapeutic such as, biologics and small molecule drugs, including but not limited to: angiogenesis inhibitors (e.g., pazopanib), antibiotics (e.g., penicillins, cephalosporins, carbapenems, macrolides, aminoglycosides, quinolones (e.g., fluoroquinolones), sulfonamides, tetracyclines), anti-inflammatories (e.g., nonsteroid antiinflamatory drugs (NSAIDS) (e.g., celecoxib), cyclooxygenase (COX) inhibitors (e.g., naproxen, diflupredante), Beta-blockers (e.g., propranolol), calcium channel blockers (e.g., verapamil), chemotherapeutics (e.g., tyrosine-kinase inhibitors (e.g., gleevec), cytotoxic antibiotics—(e.g., bleomycin), topoisomerase inhibitors (i.e., topotecan), hormones (e.g., estrogen, testosterone, human growth hormone, prolactin), immunosuppressants (e.g., cyclosporine), metabolic regulatory modalities (e.g., insulin), pain medications (e.g., narcotics, NSAIDS, opioids), psychiatric drugs (e.g., antidepressants, antipsychotics, mood stabilizers), ophthalmic medications (e.g., carbonic anhydrase inhibitors—brinzolamide, prostaglandin analogues), steroids (e.g., progestogens—progesterone, corticosteroids, mineralocorticoids-aldosterone, glucocorticoids—cortisol, androgens—testosterone, estrogens—estrogen), stem cells (e.g., burn wound healing, cancer therapy), gene therapies, delivery of viral vectors (e.g., construct delivery methods).

EXAMPLES

Example 1—Synthesis of Biodegradable Non-Gelling Amphilic Pentablock Co-Polymer (PTSsol)

In this example, a pentablock co-polymer having a PEG-PCL-PLA-PCL-PEG block configuration was prepared.

For synthesis, a polyethylene glycol-polycaprolactone (PEG-PCL) diblock copolymer was synthesized by ring opening polymerization of ε-caprolactone with monomethoxy polyethylene glycol (m-PEG) using tin octoate as a catalyst. First, mPEG 2000 and ε-caprolactone were added in a round bottom flask equipped with a stir bar. Polymer was vacuum purged four times with nitrogen, followed by addition of 0.5 wt % of m-PEG and ε-caprolactone combined of tin octoate catalyst. The reaction mixture was heated to 130° C. for 36 hours under nitrogen (Step 1). Next, the resulting diblock copolymer was re-heated to 130° C. and L-lactide was added. The reaction mixture was vacuum purged four times with nitrogen followed by addition of 0.5 wt % of entire DB and lactide combined of tin octoate catalyst and the reaction mixture was heated to 130° C. for 36 hours under nitrogen (Step 2).

The resulting triblock polymer was then dissolved in dichloromethane and precipitated by addition of chilled heptanes (cooled to −78° C.). Heptane is then decanted and the precipitate was vacuum-dried to remove any residual solvents.

Then, the resulting triblock copolymer was coupled utilizing hexamethylenediisocyanate (HMDI) as a linker to prepare PEG-PCL-PLA-PCL-PEG pentablock copolymers. Coupling reaction was carried out at 80° C. for 8 hours (step 3). The resulting polymer is re-purified by precipitation and tin is scavenged. The purified amphiphilic pentablock co-polymer is stored at −20° C. Synthesis of PEG-PCL-PLA-PCL-PEG block configuration is:

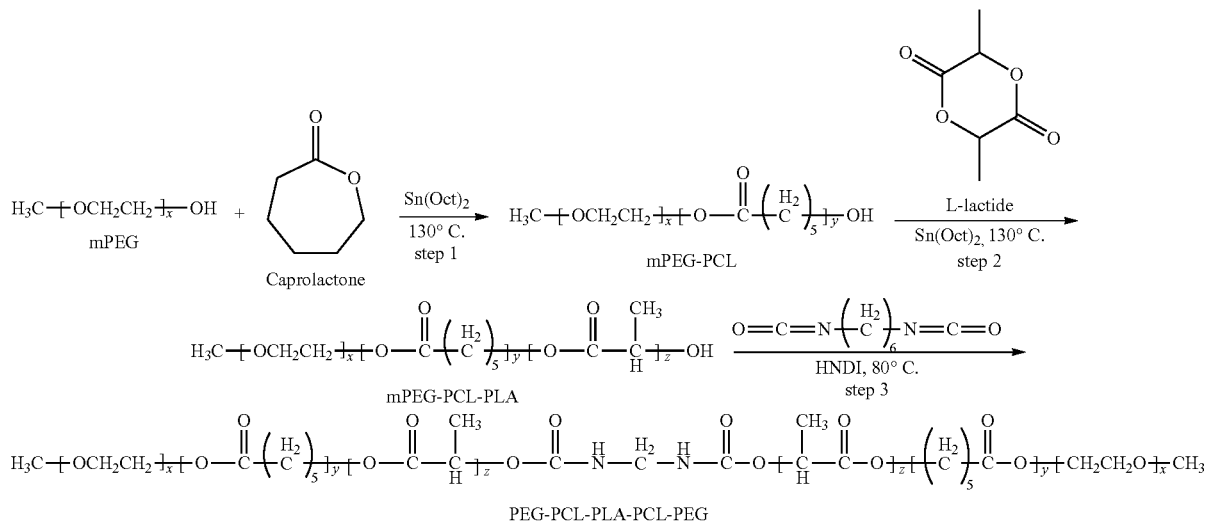

Example 2—Synthesis of Thermosensitive Biodegradable Gelling Pentablock Co-Polymers (PTSgel)

PTSgel with PEG-PCL-PLA-PCL-PEG block arrangements were synthesized as previously described in U.S. Pat. No. 8,551,531, U.S. Publication No. 20160090444, Patel et al. (Novel Thermosensitive Pentablock Copolymers for Sustained Delivery of Proteins in the Treatment of Posterior Segments Diseases, (2014) pp 1185-1200) and Patel et al. (Tailor-made pentablock copolymer based formulation for sustained ocular delivery of protein therapeutics, Invest. Ophthalmol. Vis. Sci. 55 (2014) p 4629), all of which are incorporated herein by reference in their entirety. Briefly, the diblock copolymer was synthesized by ring-opening copolymerization of ε-caprolactone with monomethoxy PEG using tin octoate as a catalyst. The resulting diblock copolymer was similarly converted to triblock by adding L-lactide. The resulting triblock copolymer was coupled utilizing hexamethylenediisocyanate (HMDI) as a linker to prepare PEG-PCL-PLA-PCL-PEG pentablock copolymers. The purified pentablock co-polymer is stored at −20° C., until used.

Example 3—Synthesis of Non-Gelling PTSsol Polymers

Several biodegradable non-gelling PTSsol polymers were synthesized, including:
  (i) (PTS-1-0GH) $PEG_{550}$-$PCL_{500}$-$PLA_{800}$-$PCL_{500}$-$PEG_{550}$ (MW=2900, PEG=37.9%)
  (ii) (PTS-120GH) $PEG_{1000}$-$PCL_{500}$-$PLA_{100}$-$PCL_{500}$-$PEG_{1000}$ (Mw=4000, PEG=50.0%)
  (iii) (PTS-121GH) $PEG_{2000}$-$PCL_{500}$-$PLA_{1000}$-$PCL_{500}$-$PEG_{2000}$ (Mw=6000, PEG=66.6%)
  (iv) (PTS-123GH) $PEG_{5000}$-$PCL_{500}$-$PLA_{1000}$-$PCL_{500}$-$PEG_{5000}$ (Mw=12000, PEG=83.3%)
  (v) (PTS-302GH) $PEG_{475(400+550\ in\ 1:1\ ratio)}$-$PCL_{500}$-$PLA_{250}$-$PCL_{500}$-$PEG_{475}$ (MW-2200, PEG=43.2%)

The polymers used herein (e.g., gelling polymers: 101GH (MW: 3,000 Da), 10GH (MW: 3,100 Da), 102GH (MW: 3,300 Da), 103GH (MW: 3,600 Da), 113GH (MW: 3,500 Da), 122GH (MW: 3,500 Da) and non-gelling polymers: 1-0GH (MW: 2900 Da), 120GH (MW: 4,000 Da), 121GH (MW: 6,000 Da), 123GH (MW: 12,000 Da)) may be constructed with different block sizes of m-PEG, PCL and PLA with PLA in the center of the molecule (m-PEG-PCL-PLA-PCL-PEG-m). The molecular weight ranged between 2200-12,000 Da, with a gradual increase in the hydrophobicity of molecules for gelation polymers, and an increase in hydrophilicity for non-gelling polymers. For gelling polymers, the objective was to vary molecular weights and hydrophobic-hydrophilic block ratios in the polymers to achieve modulation of drug release. For aqueous polymers, the objective was to vary molecular weights and hydrophobic-hydrophilic block ratios in the polymers to achieve hydrophobic active agent solubility while maintaining an aqueous composition that does not visibly gel at body temperature but becomes slightly more viscous to extend contact time and hence provide higher drug penetration in the tissue/organ, it is applied to.

Without wishing to be bound by theory, it is believed that the liquid amphiphilic pentablock co-polymer formulation described herein, when applied topically to eye surprisingly becomes bioadhesive or viscous (possibly without blurring), significantly increases contact time (e.g., 1-48 hours and longer) with ocular surface and hence allows higher drug penetration into the eye. Another advantage is that the liquid pentablock co-polymer formulation described herein can include small particles (<1 μm size is diameter, e.g., 10-200 nm), likely forming micelles which also help improve drug penetration into the eye. Small particle size because of their size and nature can avoid elimination by phagocytosis and are able to penetrate a cellular layer much more easily and hence increase in drug concentration. Indeed, as measured by DLS (see Example 12), particle size diameter can be <1 μm and preferably <200 nm and more preferably <100 nm and most preferably <30 nm. When applied topically to the eye, PTSsol may be able to deliver drugs to the back of the eye in sufficient concentration to be of therapeutic value.

As such, both the bioadhesive property of the polymer which increases contact time and the increased cellular penetration due to its small particle size composition make the formulations disclosed herein unique in resulting higher concentrations in the target tissue/organ by simple topical application. Conventional sustained release formulations are either mucoadhesive or mucopenetrating, not both. The pentablock PTSsol formulations disclosed herein unexpectedly have both properties. Due to small particle size of amphiphilic nature, which would easily disperse in aqueous formulation without the help of organic solvents or sonication etc., evade elimination by immune system, high loading capacity of hydrophobic and/or hydrophilic drug, biocompatible and biodegradable, mucoadhesive and muco-penetratable nature, this results in a very unique sustained drug release formulation including but not limited to for topical, dermal, intravitreal or parenteral applications.

Figure 2:
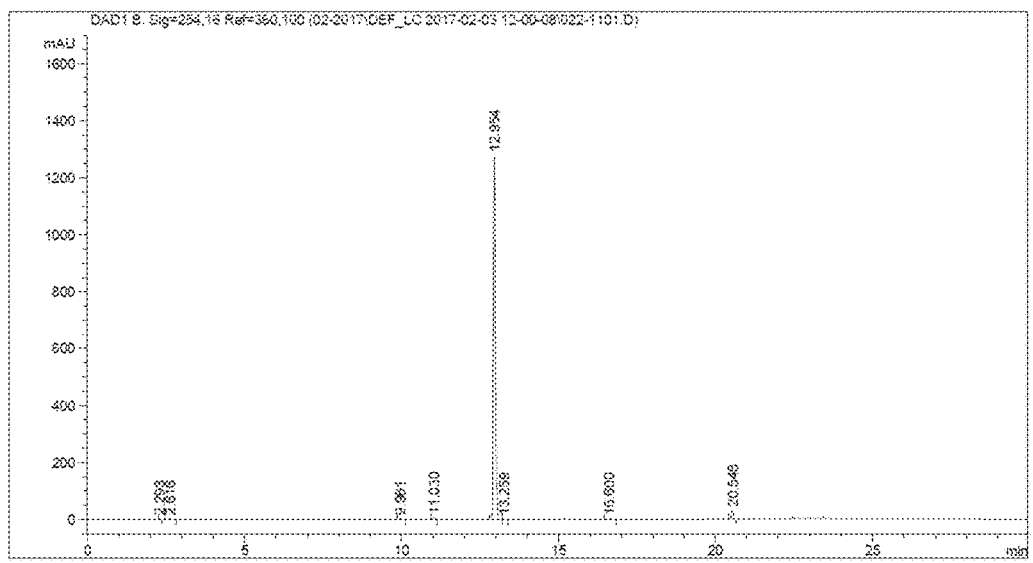
FIG. 2 shows stability by HPLC analysis (96.9%), of 2.5% Brinzolamide prepared in PTS 1-0GH and stored for 8 weeks at 4° C.
Figure 3:
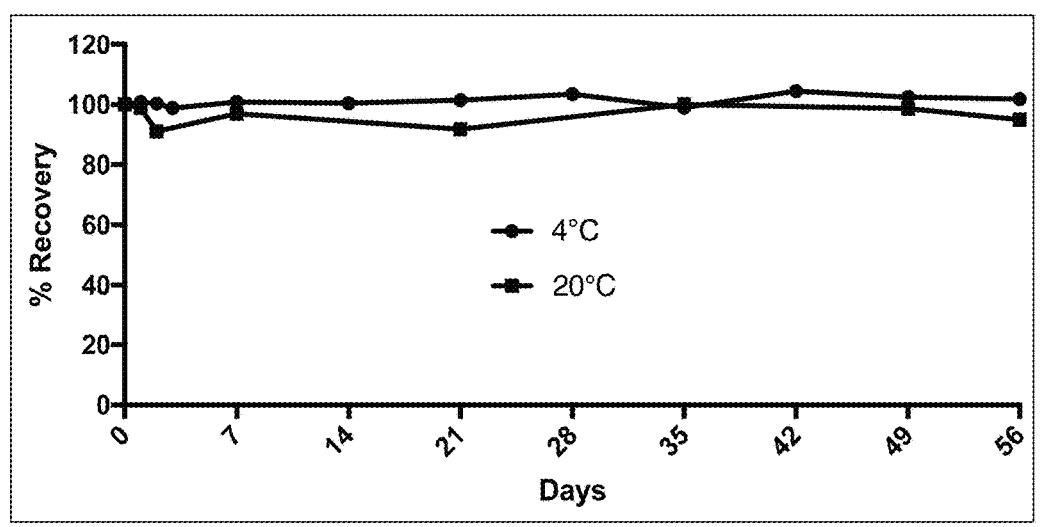
FIG. 3 shows stability of 1% Brinzolamide in PTS 1-0GH stored ure at 4° C. and 20° C. for 8 weeks (analyzed by HPLC analysis to be 93-100%).

Example 4—Difficult to Formulate Hydrophobic Active Agent Aqueous Compositions Using PTS 1-0 GH or PTS121 GH Polymer In this example, the polymer PTS1-0 GH was used to formulate aqueous compositions of difficult to suspend hydrophobic active agents. Hydrophobic active agents that are difficult to formulate in aqueous compositions are typically formulated as emulsions or suspensions. Using PTS polymer solutions (PTSsol), these difficult to formulate hydrophobic drugs can form aqueous compositions at significantly high drug concentrations, as clear liquids in hydrophilic PTSsol dispersions, to generate a useful topical formulation. For example, a 10% PTS1-0GH PTSsol was used to dissolve up to 1% cyclosporine and up to 2.5% brinzolamide, resulting in clear liquids. The PTSsol formed a stable formulation, stored at room temperature or refrigerated at 4° C., remained clear up to 8 weeks of testing. Higher concentrations for cyclosporine or brinzolamide are feasible. Similarly, PTSsol for 0.5% celecoxib was prepared in 10% PTS121GH in PBS buffer at pH 7.4. Referring to FIG. 1, left panel, a formulation of 1% cyclosporine and up to 2.5% brinzolamide were prepared in clear aqueous solutions, which remained stable over 8 weeks. Referring to FIGS. 2 and 3 the stability of 2.5% brinzolamide in 25% 1-0 GH polymer dispersion in PBS at pH 7.4 was analyzed over 8 weeks, using HPLC.

Example 5—Difficult to Formulate Hydrophobic Active Agent Aqueous Compositions Using PTS113GH or PTS122GH and PTS 121GH Polymers In this example, the polymer PTS113 GH and PTS122 GH was used to formulate aqueous compositions of especially difficult to suspend hydrophobic active agents. Especially hydrophobic active agents are difficult to formulate in aqueous compositions and may not directly dissolve in hydrophilic polymers (PTSsol), such as 121 GH. For example, difluprednate, a difficult to suspend active agent, does not readily dissolve in PTS121 GH polymer. However, difluprednate can first be dissolved in very small amounts of relatively hydrophobic gelling polymer, such as 113 GH or 122 GH to form a solution/dispersion, which is then subsequently mixed with PTS121 GH to maintain the aqueous formulations at body temperature. Using this method, stable aqueous formulations of up to a 0.1% difluprednate were achieved. Referring to FIG. 1, right panel, a formulation of 0.07% and 0.1% difluprednate were prepared as clear aqueous solutions.

Example 6—Formulation of Aqueous Compositions Containing Hydrophilic and Hydrophobic Active Agents In this example, aqueous compositions containing hydrophilic and hydrophobic active agents are formulated using PTSsol polymers. First, a hydrophobic active agent is dissolved into PTSgel (e.g., PTS 113 GH or PTS122 GH polymers as described in Example 5) followed by addition of hydrophilic non-gelling polymer, PTS121GH to form a PTSsol aqueous formulation. Second, the hydrophilic active agent such as IgG is then mixed into the PTSsol aqueous formulation containing the hydrophobic active agent. The resulting aqueous composition contains a stable formulation of hydrophilic and hydrophobic active agents.

Example 7—Artificial Tear Composition Using PTS121 GH Polymers

Figure 4:
FIG. 4 illustrates a visibly clear formulation of exemplary PTSsol artificial tears containing 1-20% of PTS 121GH non-gelling polymer. The formulation stored at room temperature remained visibly clear for 21 days after preparation.
Figure 4:
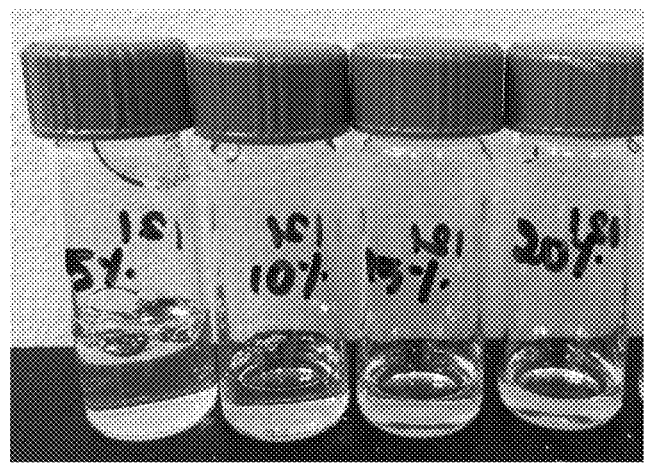

In this example, an artificial tear composition using PTSsol polymers was generated. PTS solutions are clear, bioadhesive, biocompatible, and biodegradable polymers ideal for sensitive medical applications, such as preparing artificial tears for relieving eye discomfort caused by dry eye. Due to increase in viscosity of PTSsol at body temperature, the polymer remains at the surface of which they are applied to for an extended period of time. For example, 5-20% PTS 121GH polymers were prepared in PBS at pH 7.4 as vehicle PTSsol, with no active agent. The formulations remained clear for 21 days stored at room temperature as well as at 4° C. The 121GH PTSsol polymer aqueous dispersions are ready to be tested in healthy animals and in disease models. Referring to FIG. 4, formulations of artificial tears consisting of 5, 10, 15, and 20% 121GH polymer were prepared as clear aqueous solutions, which remained visibly clear over 21 days. Additional excipients can be added to the formulation as desired.

It should be noted that artificial tear preparation can be used as a lubricant for joints or wound cover or adhesive and other similar applications.

Example 8. PTSsol Remains Liquid

Figure 5A:
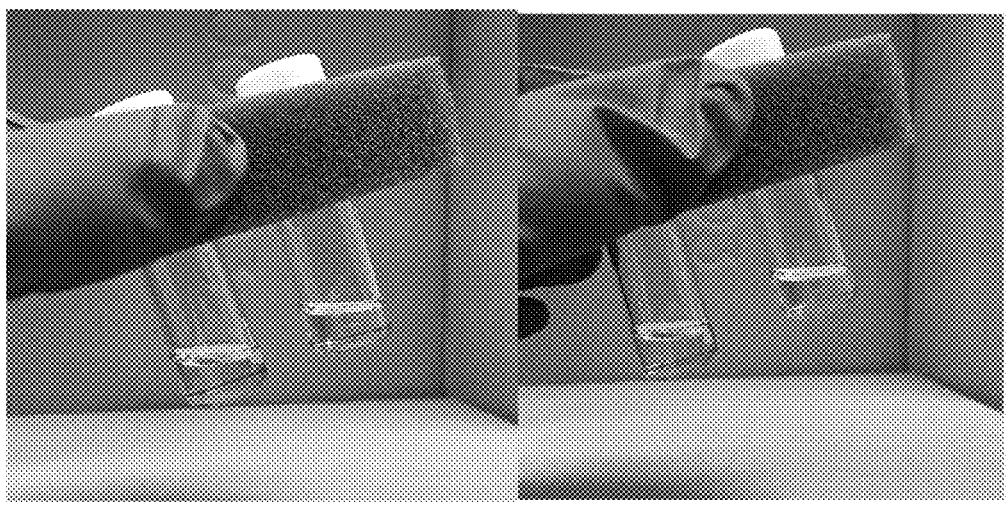
FIGS. 5A-5B show exemplary PTSsol are liquid at both 4° C. and at body temperature (about 37° C.).
Figure 5A:
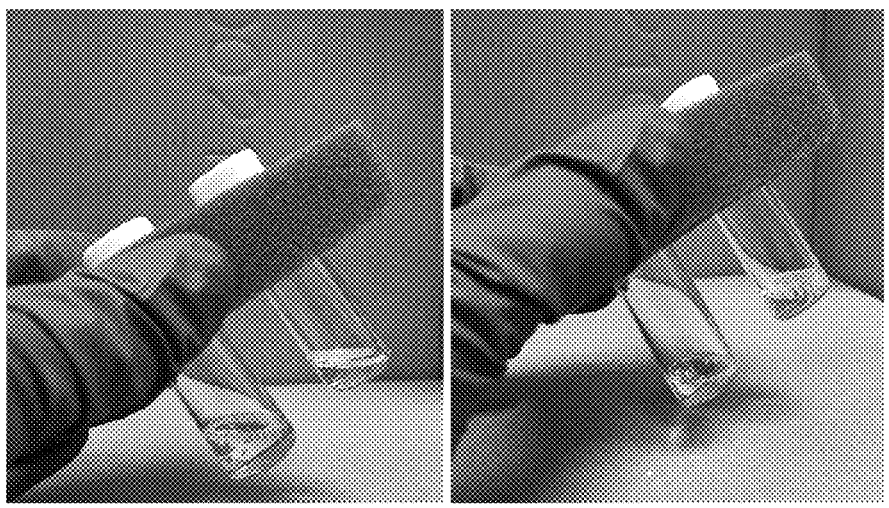
Figure 5B:
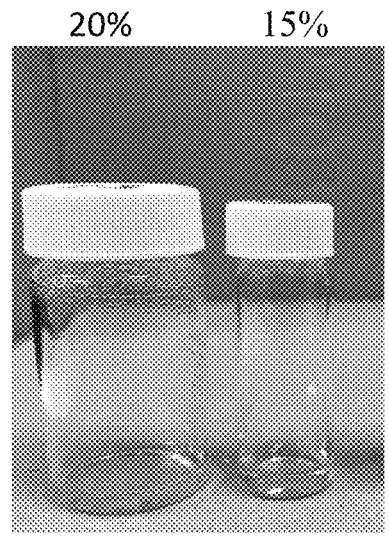
Figure 5B:
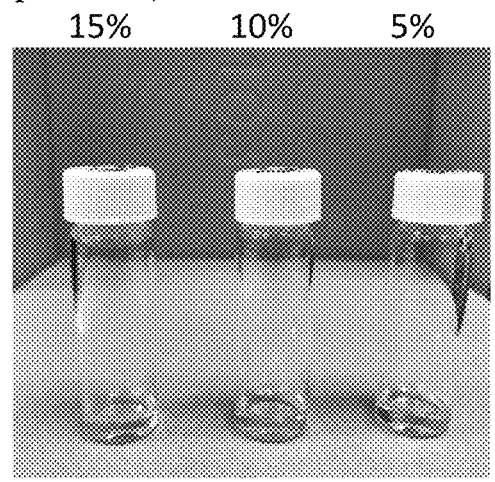

FIGS. 5A-5B show that exemplary PTSsol are liquid at both 4° C. and at body temperature (about 37° C.).

Example 9—Inhibition of Polymer Gelation

In this example, PTSsol polymers were used to inhibit the gelation of gelling polymers (PTSgel). For example, PTSsol polymers do not gel instantly at body temperature, but also when added, in some amounts to an aqueous solution of the gelling pentablock co-polymers, prevent gelling of the polymers which otherwise inherently would gel instantly. A volume of 250 uL of PTS121GH polymer was added to 4 mL of 25% PTS103GH or PTS113GH solution. As a result of the addition of 250 uL of 121GH, neither the PTS103 GH nor PTS113 GH solution achieved instant gelation at 37° C. The inhibition of polymer gelation is extremely useful for solubilizing certain drugs that would need a gelling hydrophobic polymer to dissolve but when mixed with non-gelling hydrophilic polymer will remain liquid at body temperature (about 37° C.) for significantly long periods (such as about 4 hours or longer).

Example 10—NMR Analysis of PTS 121GH $^1$H-NMR Analysis.
Purity, molecular structure and molecular weight (Mn) of the PTSsol were analyzed utilizing a Mercury 300-MHz NMR spectrometer. $^1$H-NMR spectrograms were recorded by dissolving the polymers in deuterated chloroform ($CDCl_3$).

Figure 6:
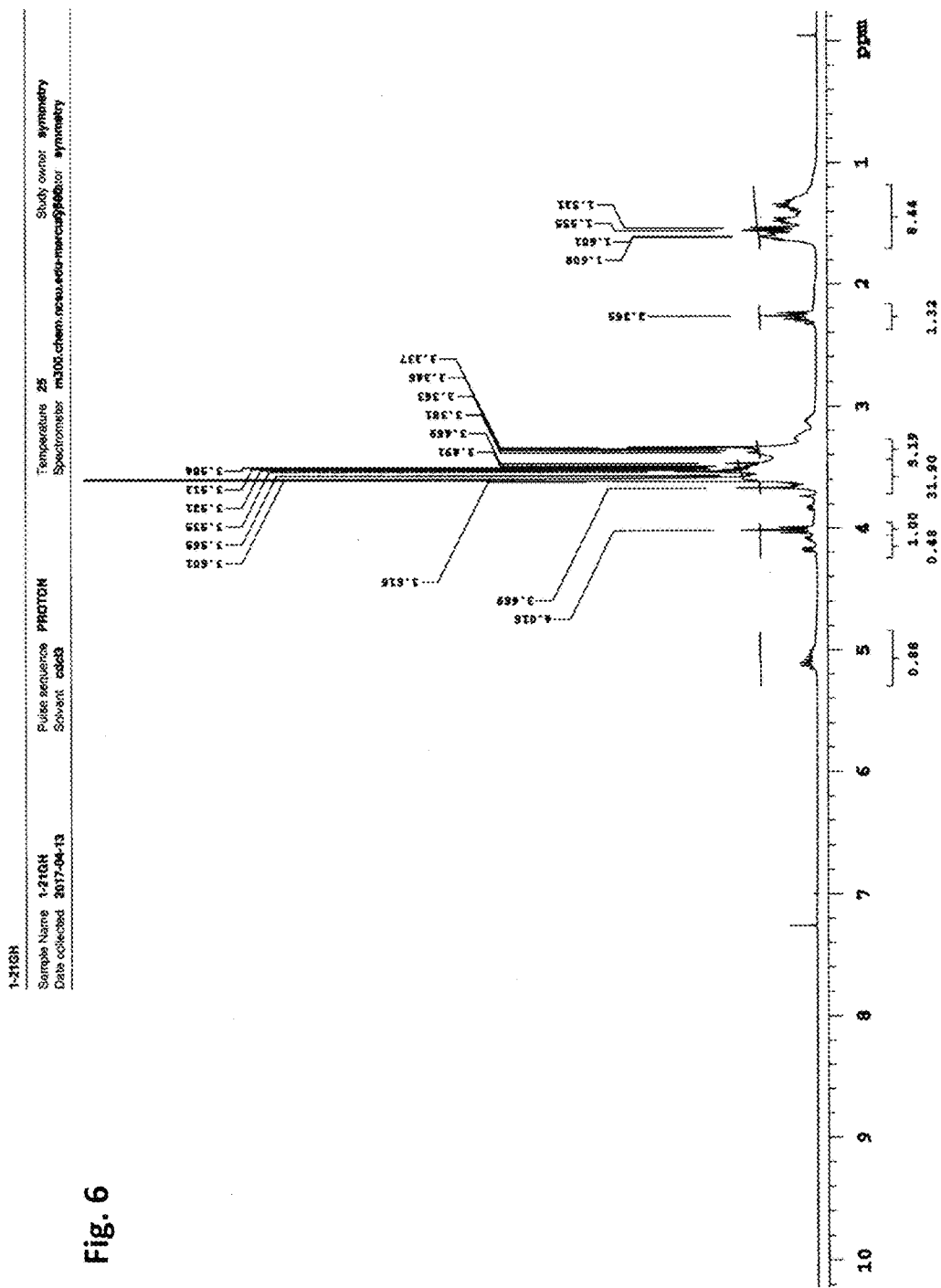
FIG. 6 shows NMR of PTS 121GH.

A Mercury 300-MHz NMR spectrometer was employed to characterize the pentablock co-polymers. FIG. 6 depicts $^1$H-NMR spectra of PTS121GH in deuterated chloroform. As described in FIG. 6, typical $^1$H-NMR characteristic peaks were observed at 1.55, 2.30 and 4.04 δ ppm representing methylene protons of —(CH$_2$)$_3$—, —OCOCH$_2$—, and —CH$_2$OOC— of PCL units, respectively. A sharp peak at 3.64 δ ppm was attributed to methylene protons (—CH$_2$CH$_2$O—) of PEG. Typical signals at 1.50 (—CH$_3$) and 5.17 (—CH—) δ ppm were assigned for PLA blocks. Whereas, a peak at 3.36 δ ppm was denoted to terminal methyl of (—OCH3-) of PEG. The [EO-[CL]-[LA] molar ratios of final products were calculated from integrations of PEG signal at 3.36 δ ppm, PCL signal at 4.04 δ ppm and PLA signal at 5.17 δ ppm. PEG signal at 3.36 δ ppm was applied for the calculation of molar ratio of various blocks within the pentablock co-polymer. Estimated molecular weight, calculated using NMR, was close to theoretical feed ratio.

Example 11—GPC Analysis of PTS 121GH

Molecular weights (Mn and Mw) and polydispersity of polymers were examined by Gel Permeation Chromatography (GPC) analysis. Briefly, 20 mg of polymer was dissolved in 1 mL of tetrahydrofuran (THF). Polymer samples were separated on two oligopore columns (Agilent, Santa Clara, Calif.) connected in series and maintained at 40° C. Solvent THF at the rate of 0.5 mL/min was utilized as eluting solvent. Samples were analyzed on Wyatt technologies MINI DAWN instrument (S. No. 528-T) connected to OPTILAB DSP interferometric refractometer, using ASTRA 6 software.

Figure 7:
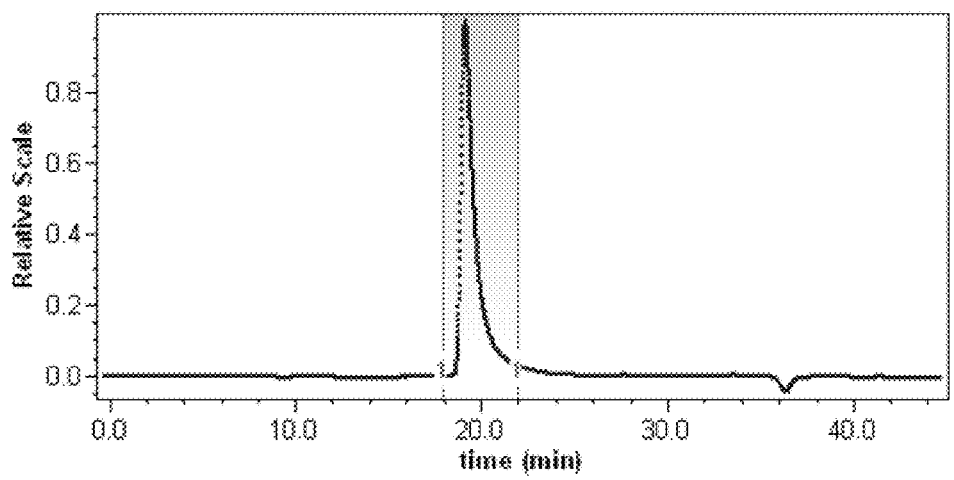
FIG. 7 shows GPC analysis of PTS 121GH. Polydispersity (Mw/Mn): 1.053 (±3.986%).

Molecular weight (Mw and Mn) and polydispersity of polymers were determined by GPC. A typical GPC chromatogram of 121GH pentablock co-polymer is shown in FIG. 7. A single peak for the polymer was observed suggesting unimodal distribution of molecular weight and absence of any other homopolymer block such as PEG, PCL or PLA. Polydispersity (PDI) for the co-polymers was 1.053 indicating narrow distribution of molecular weights.

Example 12—DLS Analysis of PTS 1-0 GH

Figure 8:
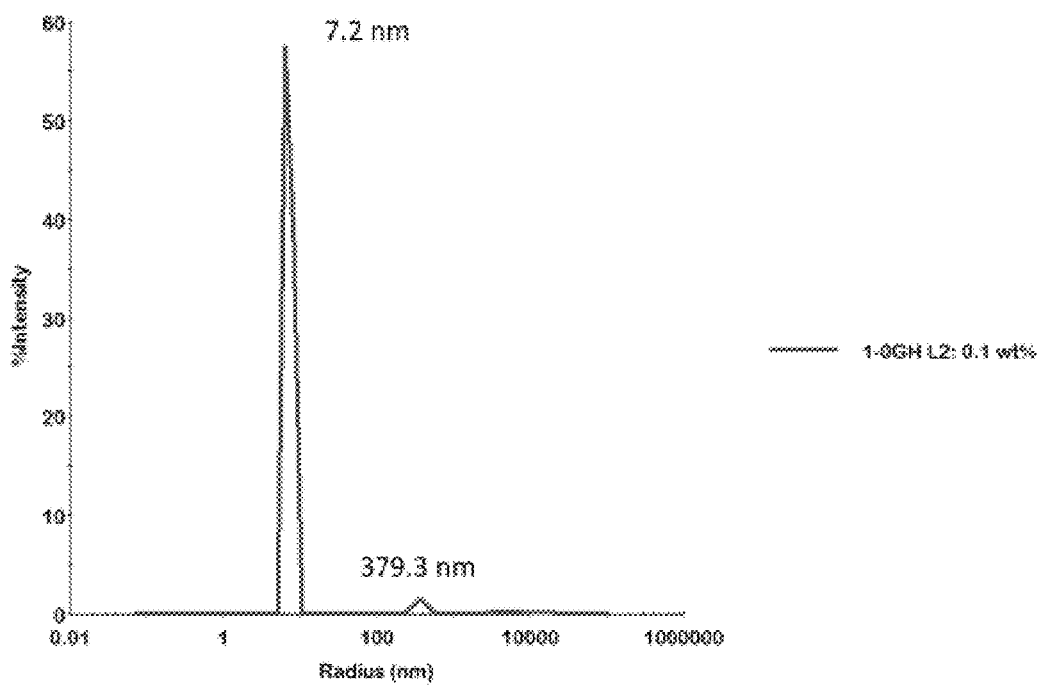
FIG. 8 shows Dynamic Light Scattering (DLS) of PTS 1-0GH dispersion in water (1 mg/mL).

Preparation and Size Characterization of Pentablock Copolymers Using Dynamic Light Scattering (DLS): An amphiphilic pentablock co-polymer (1-0GH) was dissolved at 1 mg/mL in HPLC pure water and stored at 4° C. until analyzed. The solution was analyzed for particle size by DLS with a Wyatt 233-MOB Mobius instrument (Mw-R model: Globular proteins). The analysis was performed at an angle of 163.5° at 20° C. The mean radii were obtained after five runs of ten acquisitions. The results are shown in FIG. 8. The particle size diameter measured by DLS for PTS 1-0GH was 14.4 nm in diameter (7.2 nm radius).

Example 13—Brinzolamide Formulation (2.5%) in PTSsol and 8-Week Stability

PTSsol polymer dispersion provided a stable vehicle that resulted in a clear aqueous solution of a relatively high concentration (2.5%) of a commonly used, poorly soluble drug, brinzolamide (BRZ) in PTSsol 1-0GH-L2 (25% in PBS, pH 7.4). This formulation was tested for lowering potential of TOP and tolerability in normotensive dogs. Formulated BRZ was analyzed using an HPLC method described below.

HPLC Method
Chromatographic Conditions
Column: Phenomenex Kinetex C18, 5 μm, 100 Å (250 mm×4.6 mm)
Mobile Phase:

| Time (min) | A (%) | B (%) |
|---|---|---|
| 0 | 90 | 10 |
| 5 | 90 | 10 |
| 10 | 50 | 50 |
| 15 | 50 | 50 |
| 20 | 10 | 90 |
| 25 | 10 | 90 |
| 27 | 90 | 10 |
| 30 | 90 | 10 |

Buffer A: 0.01M Ammonium acetate buffer pH 3.8
Preparation: Weigh 0.7708 g of Ammonium acetate and dissolve it in 1 L HPLC water. Adjust the pH to 3.8 using acetic acid.
Buffer B: HPLC grade methanol
Flow rate: 1000 μL/min
Column temperature: 25° C.
Wavelength: 254 nm
Injection volume: 10 μL HPLC analysis of formulated drug showed that Brinzolamide was stable at 4° C. for the tested period of up to 8 weeks. Specifically, FIG. 2 shows Brinzolamide (2.5%) in PTSsol (PTS 1-0GH, 25% in PBS, pH 7.4), after 8 weeks of storage at 4° C. (peak with RT 12.954 is Brinzolamide).

Example 14—Stability Testing of Brinzolamide Formulation at 4° C. and at Room Temperature (about 20° C.)

In a parallel experiment, stability of formulated Brinzolamide (1%) in PTSsol (PTS 1-0 GH, 25% in PBS, pH 7.4) was tested for stability, stored refrigerated (about 4° C.) or under ambient conditions (about 20° C.).

FIG. 3 shows stability of Brinzolamide (1%) formulated in PTSsol (PTS 1-0GH, 25% in PBS, pH 7.4), after 8 weeks of storage in the refrigerator (about 4° C.) or under ambient conditions (about 20° C.).

Example 15—Ocular Surface Retention of NIR-IgG (Formulated in PTSsol) in Mice

All animal protocols were conducted according to the ARVO Statement for the Use of Animals in Ophthalmic and Vision Research.

A PTSsol polymer 1-0GH-L2 (MW 3100 DA) was synthesized, which remained in liquid phase at room temperature and at 37° C. Corneal retention time was evaluated by applying PTSsol containing NIR-labeled IgG (IRDye800CW, LICOR Biosciences, Lincoln, Nebr.) to the corneal surface of mice and monitored by in vivo imaging (IVIS, Xenogen, Alameda, Calif.).

IgG was labeled with a near-infrared (NIR) dye (IRDye 800CW by LICOR Biosciences, Lincoln, Nebr.). NIR-IgG in a buffer (PBS-phosphate buffered saline, pH 7.4) or in PTSsol solution (25% polymer dispersion in PBS, pH 7.4%) was made by adding 200 uL of PTSsol dispersion or PBS to 0.2 mg of lyophilized NIR-labeled IgG, resulting in an 0.8 mg/mL (0.08%) final NIR-IgG concentration. After gentle vortexing, the solutions were stored at 4° C. until being used within 24 hours.

Mice (n=3/group) were dosed with PTSsol solution or PBS solution with both containing NIR-IgG. A volume of 2 uL of the NIR-IgG solution was applied to the right cornea of anesthetized mice (1-3% isoflurane in $O_2$) for serial in vivo imaging (IVIS, Xenogen, Alameda, Calif.) using Indocyanine Green (ICG) settings. NIR-IgG fluorescence was quantified using the IVIS imaging software automatic region of interest (ROI) setting to calculate the radiant efficiency of the NIR-IgG signal on the corneal surface of each eye. Mice were maintained under general anesthesia for the first 15 minutes of imaging, then allowed to recover between each subsequent imaging session. Images were obtained pre-application (time 0), then 1, 5, 10, 15, 30, 60, 90, and 120 minutes post-application, and every hour up to 12 hours, if fluorescence signal was still present. If signal was still present at the 12-hour time point, additional imaging was performed the following morning at 21 hours post-application.

Figure 9:
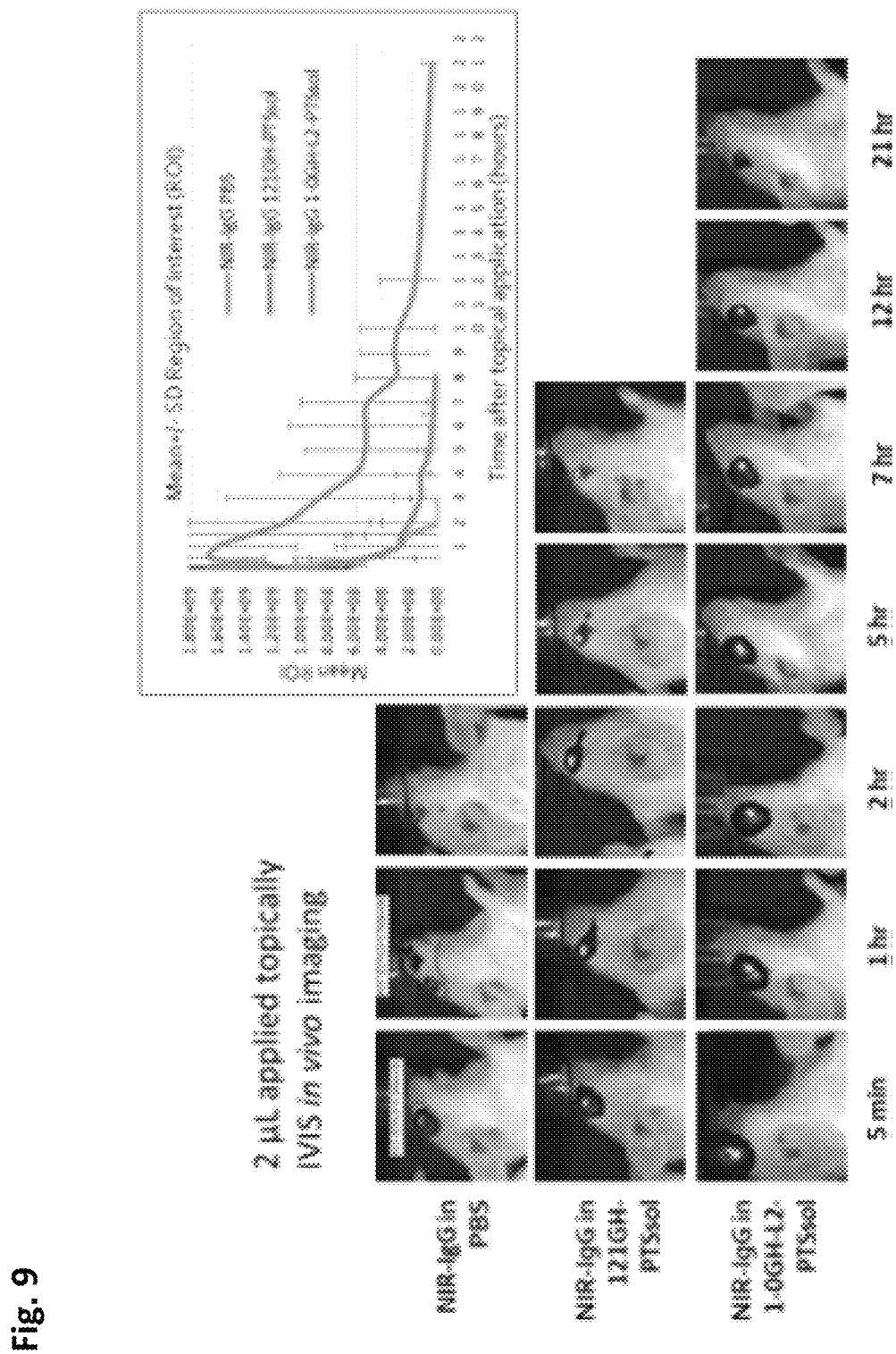
FIG. 9. shows sustained release of NIR-IgG for >21 h after topical ocular application of NIR-IgG in PTSsol in mice.

NIR-IgG in PBS was barely detected 2 hours post application on the ocular surface of mice, whereas NIR-IgG in PTSsol using 1-0GH polymer remained on the ocular surface for >21 hours (FIG. 9). Also, the PTSsol formulation was well tolerated, without signs of inflammation at any time point.

Specifically, FIG. 9 shows in vivo imaging of NIR-IgG in PBS or PTSsol after topical ocular application in the right eye in mice. Retention of NIR-IgG on ocular surface: less than 2 h in PBS (Top row); greater than 7 hours in PTSsol 121GH (Middle row) and greater than 21 hours in PTSsol 10-GH-L2 (bottom row). Graph: Region of interest (ROI) concentration intensity calculated by imager (N=3 mice per group).

The experiment clearly demonstrates using a labeled IgG protein in the PTSsol, that the IgG was retained on the ocular surface or cornea for >21 hours. This suggests that once a day topical application of drugs (Biologics or chemical) for anterior segment of the eye is feasible.

Example 16—Dosing of Brinzolamide in PTSsol, Tolerability, IOP Monitoring in Normotensive Dogs All animal protocols were conducted according to the ARVO Statement for the Use of Animals in Ophthalmic and Vision Research. Six normotensive mixed-breed dogs were dosed 3 consecutive days with PTSsol vehicle qd, Brinzolamide (BRZ) 2.5% in PTSsol (25% PTS 1-0 GH-L2 in PBS buffer, pH 7.4) qd, and commercial BRZ 1% (Azopt) tid. IOP was measured at 7 am and 3 pm for each treatment day and at 7 am for two days following treatment. Ocular exams were performed daily to monitor tolerability.

All IOP measurements were obtained by rebound tonometry (TonoVet®, icare, Helsinki, Finland) with a disposable probe held horizontally, 4-5 mm from the corneal surface. Three independent IOP readings were obtained from each eye, and the mean of the three averaged readings was used at the IOP for each time point. The same instrument as used throughout the acclimation and experiment periods. Each dog was gently restrained for readings without use of sedatives. Baseline IOP was measured in six normotensive, for three consecutive days. The left eye (OS) in all dogs, in all periods served as the treated eye and the right eye (OD) served as the untreated control eye. Dogs were dosed with 50 uL of an individual solution to the corneal surface for three consecutive days, with four untreated days between treatments.

As evident from the data presented in the Table below and FIG. 10, by day 3 of dosing, IOP was significantly lower in Azopt tid and 2.5% BRZ in PTSsol qd dosed eyes compared to vehicle or baseline at both 7 AM and 3 PM (P<0.014). On day 5, 48 hours after dosing, IOP remained significantly lower in eyes dosed previously with 2.5% BRZ PTSsol qd compared to those dosed with Azopt tid (P=0.036).

TABLE

Mean +/− SEM difference in intraocular pressure (IOP) between OS (dosed) and OD (not dosed)

| | Day and time of IOP measurement | | | | | | | |
|---|---|---|---|---|---|---|---|---|
| Group | Day 1 7 AM* | Day 1 3 PM | Day 2 7 AM* | Day 2 3 PM | Day 3 7 AM* | Day 3 3 PM | Day 4 7 AM** | Day 5 7 AM** |
| Baseline | −0.34 ± 0.6 | −0.93 ± 0.3 | 0.38 ± 0.6 | −0.13 ± 0.4 | −0.67 ± 1.0 | −0.2 ± 0.7 | — | — |
| PTSsol vehicle (qd) | −0.93 ± 0.3 | −0.13 ± 0.4 | −0.2 ± 0.7 | −0.73 ± 0.4 | 0.2 ± 0.4 | −0.47 ± 0.3 | −0.27 ± 0.6 | −0.13 ± 0.4 |
| Azopt (tid) | −0.33 ± 0.7 | −2.2 ± 0.6$^a$ | −2.0 ± 1.0 | −2.6 ± 0.4$^b$ | −2.3 ± 0.5$^c$ | −1.6 ± 0.7$^d$ | −1.4 ± 0.5 | 0.47 ± 0.5 |
| 2.5% BRZ in PTSsol (qd) | 1.1 ± 0.4 | −3.4 ± 1.2$^a$ | −1.3 ± 0.9 | −1.3 ± 2.2 | −3.1 ± 0.3 | −2.4 ± 0.4$^d$ | −2.1 ± 0.2 | −1.3 ± 0.4$^f$ |

Figure 10:
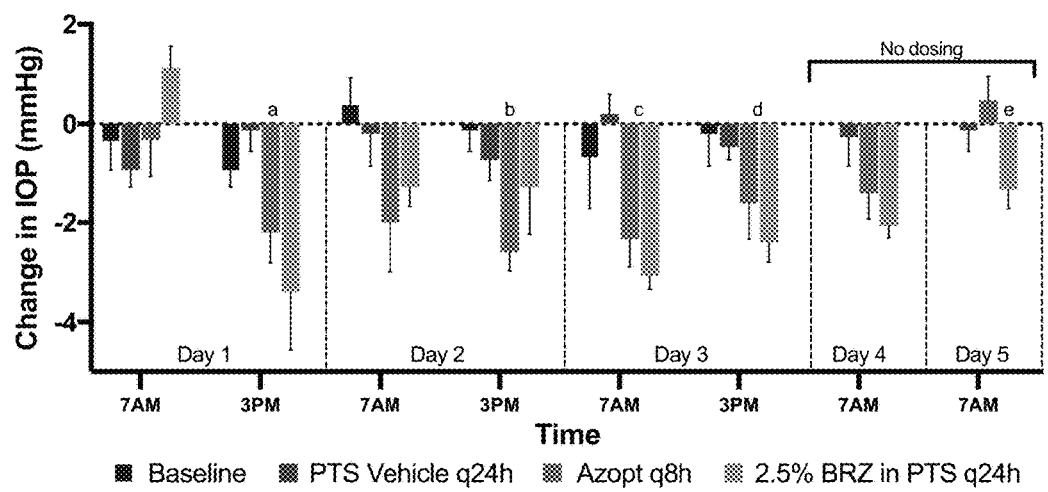
FIG. 10 shows PD effect for TOP reduction in normotensive dogs after one application a day of BRZ 2.5% (prepared in PTSsol), compared against Azopt® 1%, three times a day.

*prior to first treatment of the day;
**no treatments on days 4 and 5
BRZ—brinzolamide;
qd - dosed once a day (following IOPs at 7 AM),
tid - dosed every 8 hours FIG. 10 shows IOP measurement in normotensive mixed breed dogs (n=6).

Ocular examinations using a slit-lamp biomicroscope (Sl-17, KOWA, Tokyo, Japan) and modified Hackett-Mc-Donald ocular irritation scoring were performed 30 minutes after the AM dose each day and for 2 days (in the AM) following dosing to monitor tolerability.

Topical ocular application of PTSsol vehicle qd, and PTSsol 2.5% BRZ qd were well tolerated by the dogs during 3 days of dosing and for the 2 days following dosing. On slit-lamp examination, there were no signs of conjunctival hyperemia, chemosis, or other signs of ocular inflammation in any of the dosing groups on any day.

Sustained lowering of 48 hours (and potentially longer but not yet tested) post-dosing suggests that a PTSsol of 2.5% BRZ, which was well tolerated, may allow once a day, or less frequent, dosing, for treatment of glaucoma.

A formulation containing PTSsol may be useful for sustained topical ocular drug delivery of antibiotics, antifungals, other anti-glaucoma drugs, and anti-inflammatories and other drugs as needed. Furthermore, depending on the ocular pharmacokinetics of the individual drugs, PTSsol may enhance drug delivery to the ocular posterior segment for treatment of age related macular degeneration or diabetic retinopathy, as examples.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for the use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items. "Consisting essentially of" means inclusion of the items listed thereafter and which is open to unlisted items that do not materially affect the basic and novel properties of the disclosure.

INCORPORATION BY REFERENCE

All publications and patents mentioned herein are hereby incorporated by reference in their entireties as if each individual publication or patent was specifically and individually indicated to be incorporated by reference.

The invention claimed is:

1. A liquid formulation comprising an aqueous solution of a composition for delivery of an active ingredient, the composition comprising a block polymer having the formula of PEG-PCL-PLA-PCL-PEG or PGA-PCL-PEG-PCL-PGA or PLA-PCL-PEG-PCL-PLA or PCL-PLA-PEG-PLA-PCL or PCL-PGA-PEG-PGA-PCL in the form of an aqueous dispersion, wherein the aqueous solution includes one or more of amphiphilic polymer excipients, tonicity agents, buffers, sugars selected from trehalose, mannose, D-galactose, and lactose, preservatives, co-solvents or antioxidants,
    wherein PEG is polyethylene glycol and has an average molecular weight of about 100 Da to about 10,000 Da and comprises at least 25% of the block polymer by molecular weight;
    wherein PCL is poly($\varepsilon$-caprolactone) and has an average molecular weight of about 100 Da to about 3000 Da;
    wherein PLA is polylactic acid having an average molecular weight of about 100 Da to about 5,000 Da;
    wherein PGA is polyglycolic acid having an average molecular weight of about 100 Da to about 5,000 Da; and
    wherein the polymer has a total molecular weight of about 1,500 Da to about 20,000 Da.

2. The liquid formulation according to claim 1, wherein the aqueous dispersion of the polymer is a liquid at body temperature.

3. The liquid formulation according to claim 1, wherein the block polymer is present at about 0.01 wt % to about 50 wt % of the liquid formulation.

4. The liquid formulation according to claim 3, further comprising an active ingredient that is hydrophobic.

5. The liquid formulation according to claim 1, further comprising an active ingredient admixed therein.

6. The liquid formulation according to claim 5, wherein the aqueous solution is a solution wherein water or aqueous buffer is a solvent.

7. The liquid formulation according to claim 5, wherein the active ingredient is present at about 0.01 wt % to about 50 wt % of the liquid formulation.

8. The liquid formulation according to claim 5, wherein the active ingredient is a biologic or chemical agent.

9. The liquid formulation according to claim 5, wherein the active ingredient is hydrophobic or hydrophilic, or a mixture of hydrophobic and hydrophilic ingredients.

10. An artificial tear or lubricant for joint or wound cover or adhesive comprising the liquid formulation of claim 1.

11. The artificial tear of claim 10, wherein the aqueous solution has a pH ranging from about 5.0 to about 8.0.

12. A method of delivering an active ingredient to a mammal in need thereof, comprising:
    providing the liquid formulation of claim 1 admixed with an active ingredient, wherein the block polymer is present at between about 0.01 wt % and about 50 wt % of the liquid formulation; and
    administering the liquid formulation to a mammal.

13. The method of claim 12, wherein said administering is by a topical, oral or parenteral route.

14. The method of claim 12, wherein the liquid formulation is administered to an ocular surface and provides sustained release of the active ingredient for 1-48 hours.

15. The method of claim 12, wherein the liquid formulation is administered via intravitreal or intra articular injection and provides sustained release of the active ingredient for at least 1 day.

* * * * *

UNITED STATES PATENT AND TRADEMARK OFFICE
CERTIFICATE OF CORRECTION

PATENT NO. : 10,207,003 B2
APPLICATION NO. : 15/582685
DATED : February 19, 2019
INVENTOR(S) : Poonam R. Velagaleti et al.

Page 1 of 1

It is certified that error appears in the above-identified patent and that said Letters Patent is hereby corrected as shown below:

On the Title Page

In the Assignees Field please replace "(73) Assignee: inovion, Inc., Randolph, NJ (US)" with "(73) Assignee: i-novion, Inc., Randolph, NJ (US)"

Signed and Sealed this
Seventh Day of May, 2019

Andrei Iancu
*Director of the United States Patent and Trademark Office*